United States Patent [19]

Henzi

[11] 4,247,457

[45] Jan. 27, 1981

[54] CATIONIC DYES CONTAINING AN ARYLOXY GROUP LINKED THROUGH A BRIDGING RADICAL TO A QUATERNIZED NITROGEN ATOM

[75] Inventor: Beat Henzi, Neuallschwil, Switzerland

[73] Assignee: Sandoz Ltd., Basel, Switzerland

[21] Appl. No.: 848,886

[22] Filed: Nov. 7, 1977

Related U.S. Application Data

[60] Division of Ser. No. 635,600, Nov. 28, 1975, Pat. No. 4,072,672, which is a continuation of Ser. No. 383,878, Jul. 30, 1973, abandoned.

[30] Foreign Application Priority Data

Jul. 31, 1972 [CH] Switzerland ............... 11354/72
Dec. 7, 1972 [CH] Switzerland ............... 17824/72
Feb. 5, 1973 [CH] Switzerland ............... 1618/73
Feb. 21, 1973 [CH] Switzerland ............... 2523/73

[51] Int. Cl.³ ............... C07C 103/75; C09B 29/36; C09B 29/38; C09B 31/04
[52] U.S. Cl. ............... 260/158; 260/145 R; 260/146 R; 260/146 D; 260/147; 260/148; 260/149; 260/151; 260/152; 260/154; 260/156; 260/157; 260/159; 260/162; 260/163; 260/164; 260/165; 260/177; 260/184; 260/185; 260/186; 260/187; 260/346.72; 260/377; 260/379
[58] Field of Search ............... 260/146 R, 158, 146 D, 260/154, 156, 152, 157, 159, 162, 163, 164, 165, 177, 184, 185, 186, 187, 190, 346.72, 377, 379

[56] References Cited

U.S. PATENT DOCUMENTS

| | | | |
|---|---|---|---|
| 2,972,508 | 2/1961 | Kaockenberg et al. | 260/158 X |
| 3,033,847 | 5/1962 | Sartori | 260/158 |
| 3,729,459 | 4/1973 | Hegar | 260/158 X |
| 3,732,201 | 5/1973 | Ramanathan | 260/158 X |
| 3,761,462 | 9/1973 | Moritz et al. | 260/158 |
| 3,812,093 | 5/1974 | Fisher et al. | 260/158 X |
| 3,933,787 | 1/1976 | Moser | 260/158 |
| 4,051,084 | 9/1977 | Kuhlthau et al. | 260/158 |
| 4,051,117 | 9/1977 | Kuhlthau et al. | 260/146 R |
| 4,072,672 | 2/1978 | Henzi | 260/158 X |

FOREIGN PATENT DOCUMENTS

785057 12/1972 Belgium ............... 260/158
1162665 8/1969 United Kingdom ............... 260/158

*Primary Examiner*—John Doll
*Attorney, Agent, or Firm*—Gerald D. Sharkin; Richard E. Vila; Melvyn M. Kassenoff

[57] ABSTRACT

Basic dyes, e.g., azo dyes and anthraquinone dyes, free from sulphonic acid groups which contain, a group of the formula

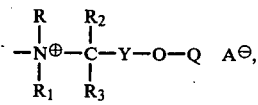

in which R and $R_1$, independently, are substituted or unsubstituted $C_{1-4}$ alkyl or are linked to form a ring, or
one of R and $R_1$ is $-NH_2$ or $C_{1-4}$ alkoxy and the other is substituted or unsubstituted alkyl,
$R_2$ and $R_3$, independently, are hydrogen or $C_{1-4}$ alkyl,
Y is a bridging group,
Q is unsubstituted or substituted phenyl, biphenylyl, naphthyl or

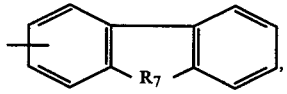

in which $R_7$ is $-S-$, $-O-$,

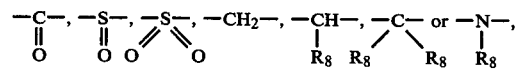

where $R_8$ is $C_{1-4}$ alkyl, and $A^\ominus$ is an anion.

These dyes are useful for the dyeing and printing of polymers and copolymers of acrylonitrile and asymmetrical dicyanoethylene as well as polyesters and polyamides modified to contain acid groups. The dyes build-up well and exhibit good pH stability and stability to boiling. The obtained dyeings are level and possess good fastness to light, wet treatments, solvents, heat treatments and cross-dyeing.

60 Claims, No Drawings

CATIONIC DYES CONTAINING AN ARYLOXY GROUP LINKED THROUGH A BRIDGING RADICAL TO A QUATERNIZED NITROGEN ATOM

This application is a division of application Ser. No. 635,600, filed on Nov. 28, 1975 and now U.S. Pat. No. 4,072,672, which is a continuation of application Ser. No. 383,878, filed on July 30, 1973 and now abandoned.

The invention relates to basic dyes free from sulphonic acid groups.

The invention provides basic dyes, free from sulphonic acid groups, which contain, as characteristic group, a group of formula T

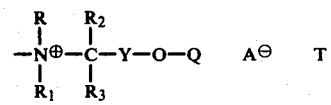

in which either R and $R_1$, which may be the same or different, each signifies an alkyl radical of 1 to 4 carbon atoms, unsubstituted or substituted by hydroxy or phenyl,
or one of R and $R_1$ signifies —$NH_2$ or $C_{1-4}$ alkoxy, the other having one of the above significances,
or R and $R_1$, together with the nitrogen atom to which they are attached, signify

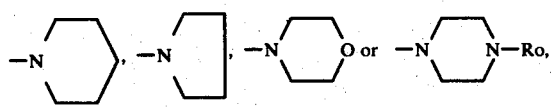

in which Ro signifies a $C_{1-4}$ alkyl or phenyl radical, or the group

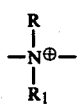

signifies, as a whole, a radical of the formula

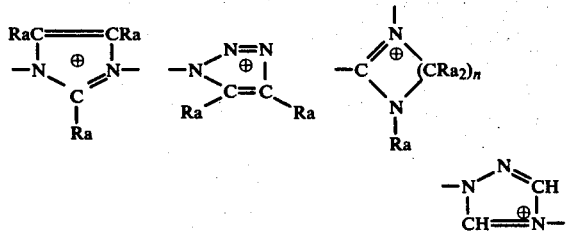

in which the Ra's, independently, signify hydrogen or alkyl of 1 to 4 carbon atoms, and n signifies 1 or 2,
$R_2$ and $R_3$, which may be the same or different, each signifies hydrogen or $C_{1-4}$ alkyl,
Y signifies

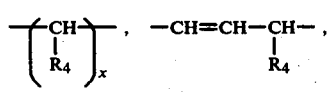

$$-C \equiv C-\underset{\underset{R_4}{|}}{CH}- \quad \text{or} \quad -\underset{\underset{R_4}{|}}{CH}-\underset{\underset{R_4}{|}}{R_5}-\underset{\underset{R_4}{|}}{CH}-\underset{\underset{R_4}{|}}{CH}-$$

in which x signifies 1 to 6, $R_4$ signifies one of the above significances of $R_2$ and $R_3$, and $R_5$ signifies —O—, —S—,

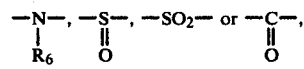

in which $R_6$ signifies hydrogen or $C_{1-4}$ alkyl,
$A^\ominus$ signifies an anion, and
Q signifies a radical of the formula

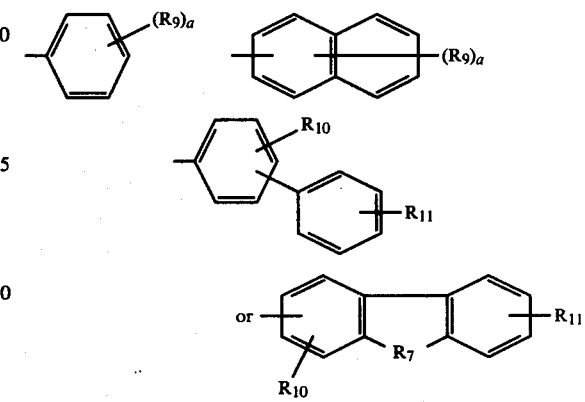

in which $R_9$ signifies hydrogen; hydroxy; halogen; alkyl or alkoxy of 1 to 4 carbon atoms, unsubstituted or substituted by halogen, hydroxy, cyano, phenyl or phenoxy; cycloalkyl of 5 or 6 carbon atoms, unsubstituted or substituted by alkyl of 1 to 4 carbon atoms; trifluoromethyl; cyano; nitro; phenoxy; naphthyloxy; phenylazo; or a radical of the formula —CORo,

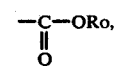

—$SO_2$—Ro, —$SO_2$—NH—Ro,

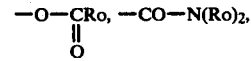

—CO—NH—Ro, —$OSO_2N(Ro)_2$, —O—$CON(Ro)_2$, —NH—CO—Ro,

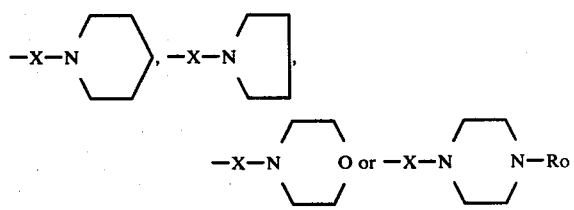

in which the Ro's, independently, signify $C_{1-4}$ alkyl or phenyl, and X signifies —CO— or —$SO_2$—, $R_{10}$ signifies hydrogen, halogen or alkyl of 1 to 4 carbon atoms, $R_{11}$ signifies hydrogen, $C_{1-4}$ alkyl, $C_{1-4}$ alkoxy, phenyl, phenoxy, halogen, —$CF_3$, —$NO_2$, —CN, —$COR_o$,

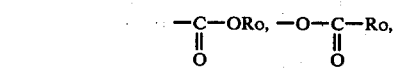

—$SO_2$—$R_o$, —$SO_2N(R_o)_2$,

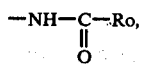

—$SO_2$—NH—$R_o$ or —CO—NH—$R_o$, a signifies 0, 1,2 or 3 or, where $R_9$ signifies halogen, 1,2,3,4 or 5, $R_7$ signifies —S—, —O—,

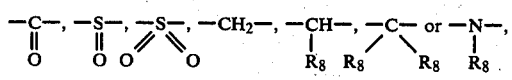

in which $R_8$ signifies $C_{1-4}$ alkyl and $R_8'$ signifies hydrogen or $C_{1-4}$ alkyl.

Preferably, R and $R_1$ each signify $C_{1-4}$ alkyl, more preferably methyl or ethyl.

Preferably, $R_2$ and $R_3$, independently, signify hydrogen or methyl, more preferably hydrogen.

Preferably, Y signifies

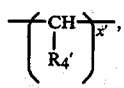

in which $R_4'$ signifies hydrogen or $C_{1-4}$ alkyl, more preferably hydrogen or methyl, most preferably hydrogen, and X' signifies 1, 2 or 3, more preferably 1, or —CH=CH—$CH_2$—, —C≡C—$CH_2$— or —$CH_2$—O—$CH_2$—$CH_2$—.

Most preferably, Y signifies —$CH_2$—.

Preferably, W signifies an unsubstituted phenyl, naphthyl, diphenylyl or dibenzofuranyl radical, or a phenyl radical substituted by halogen, preferably chlorine, $C_{1-4}$ alkyl or alkoxy, —$CF_3$, cyano or —$NO_2$, or a phenyl radical substituted by up to 5 chlorine atoms.

Most preferably, Q signifies unsubstituted phenyl or 2-naphthyl, or phenyl substituted by up to 5 chlorine atoms.

As examples of anions $A^{\ominus}$ may be given the halides, such as chloride, bromide and iodide, sulphate, disulphate, methylsulphate, aminosulphate, perchlorate, carbonate, bicarbonate, phosphate, phosphormolybdate, phosphortungstenate, phosphortungstenmolybdate, formate, benzenesulphonate, naphthalenesulphonate, 4-chlorobenzenesulphonate, oxalate, maleinate, acetate, propionate, lactate, succinate, chloroacetate, tartrate, malate, methanesulphonate and benzoate ions, and complex anions such as zinc chloride double salts, e.g. $ZnCl_3^{\ominus}$. The preferred anions are the halide, methylsulphate, $ZnCl_3^{\ominus}$, acetate and sulphate ions.

As examples of the basic dyes provided by the invention may be given the azo series of dyes of formula Ia,

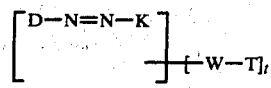

in which D signifies a diazo component radical,
K signifies a coupling component radical,
W signifies a direct bond or a bridging group,
T is as defined above, the group (s) —w—T being bound to D/or K, and
t signifies 1 or 2.

As examples of preferred compounds of formula Ia may be given the compounds of formula Iaa,

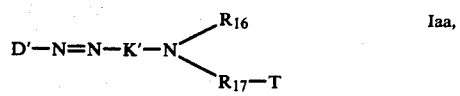

in which K' signifies a radical of formula (m) or (n),

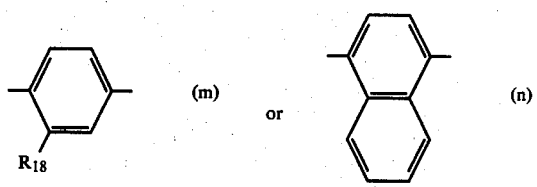

in which $R_{18}$ signifies hydrogen, $C_{1-4}$ alkyl, preferably methyl, $C_{1-4}$ alkoxy, preferably methoxy, or halogen, preferably chlorine, D'0 signifies a radical of formula (a),

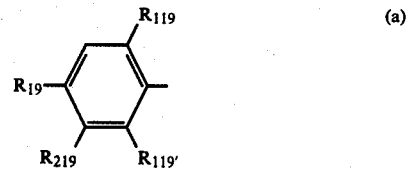

in which $R_{19}$ signifies hydrogen, nitro, halogen preferably chlorine or bromine, cyano, trifluoromethyl, $C_{1-4}$ alkylsulfonyl, preferably methylsulphonyl, phenylsulphonyl, —CO—$R_o$, $COOR_o$, —$CONHR_o$, alkyl of 1 to 4 carbon atoms, preferably methyl, alkoxy of 1 to 4 carbon atoms, preferably methoxy or —$O_2S$—$NR_{21}R_{22}$, wherein $R_{21}$ and $R_{22}$, independently, signify $C_{1-4}$ alkyl or are linked to form, together with the nitrogen atom,

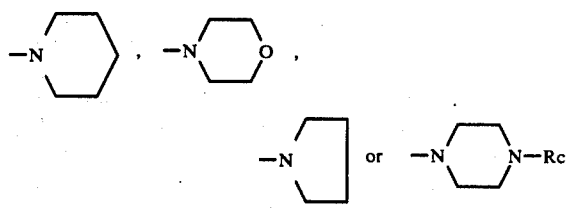

in which $R_c$ signifies $C_{1-4}$ alkyl, preferably methyl,
$R_{119}$ and $R_{119}'$, independently, signify hydrogen, nitro, halogen, preferably chlorine or bromine, cyano, $C_{1-4}$ alkyl, preferably methyl, trifluoromethyl, $C_{1-4}$ alkylsulphonyl or $C_{1-4}$ alkoxy, preferably methoxy, $R_{219}$ signifies hydrogen, halogen, preferably chlorine, nitro or cyano, with the proviso that radical (a) contains no more than 3 substituents other than halogen, a radical of formula (b) or (c)

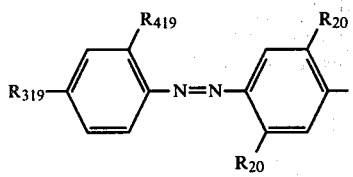
(b)

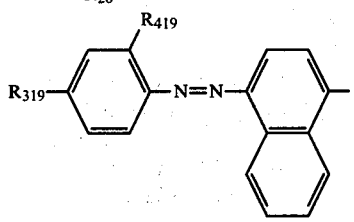
(c)

in which $R_{319}$ signifies hydrogen, halogen, preferably chlorine, nitro, cyano, trifluoromethyl or $C_{1-4}$ alkylsulphonyl, $R_{419}$ signifies hydrogen, halogen, preferably chloro, nitro, cyano, $C_{1-4}$ alkyl, preferably methyl, or $C_{1-4}$ alkoxy, preferably methoxy, the $R_{20}$'s, independently, signify hydrogen, alkyl of 1 to 4 carbon atoms, preferably methyl, or alkoxy of 1 to 4 carbon atoms, preferably methoxy, a radical of formula (d)

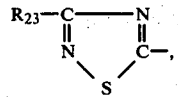

in which $R_{23}$ signifies hydrogen; phenyl; a phenyl, radical substituted by $C_{1-4}$ alkyl, preferably methyl, cyano or nitro; a $C_{1-4}$ alkylsulphonyl radical; a $C_{1-4}$ alkylsulphoxide radical; a $C_{1-4}$ alkylthio radical; halogen, preferably chlorine, or $C_{1-4}$ alkyl, preferably methyl, a radical of formula (e)

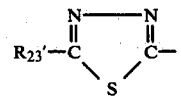

in which $R_{23}'$ signifies hydrogen; phenyl, unsubstituted or substituted by $C_{1-4}$ alkyl, preferably methyl, cyano, nitro or halogen, preferably chlorine; or $C_{1-4}$ alkyl, preferably methyl, a radical of formula (f)

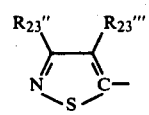

in which $R_{23}''$ signifies halogen, preferably chlorine, $R_{23}'''$ signifies cyano, —CONHRa, in which Ra signifies hydrogen or $C_{1-4}$ alkyl, or —COORo, preferably cyano, a radical of formula (g)

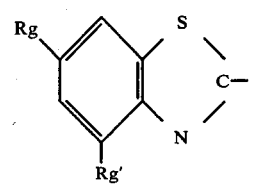
(g)

Rg signifies halogen, preferably bromine, nitro or —CO—Ro,

Rg' signifies halogen, preferably bromine, a radical of formula (h)

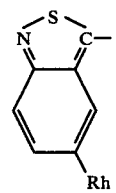
(h)

in which Rh signifies nitro, cyano, or trifluoromethyl, preferably nitro, a radical of formula (i)

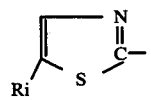

in which Ri signifies nitro or cyano, preferably nitro, a radical of formula (j)

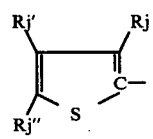

in which Rj and Rj'', independently, signify cyano, $C_{1-4}$ alkoxycarbonyl, preferably methoxycarbonyl, or —CONHRa, Rj' signifies $C_{1-4}$ alkyl, preferably methyl, or phenyl, a radical of formula (k)

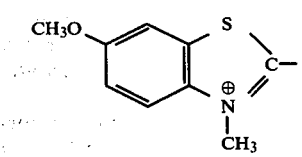

or a radical of formula (l)

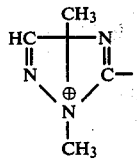

(1)

$R_{16}$ signifies hydrogen; alkyl of 1 to 4 carbon atoms, unsubstituted or substituted by halogen, hydroxy, cyano, phenyl, phenoxy, $C_{1-4}$ alkoxycarbonyl, $C_{1-4}$ alkylcarbonyloxy, $C_{1-4}$ alkoxy, benzoyloxy,

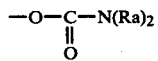

or —CON(Ra)$_2$ in which the Ra's, independently, signify hydrogen or $C_{1-4}$ alkyl; or phenyl; $R_{16}$ preferably signifying an unsubstituted alkyl radical radical of 1 to 4 carbon atoms, more preferably methyl or ethyl, $R_{17}$ signifies the

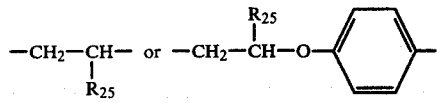

in which $R_{25}$ signifies hydrogen or $C_{1-4}$ alkyl, preferably methyl, $R_{25}$ most preferably signifying hydrogen; and T is as defined above.

In the compounds of formula Iaa, D' preferably signifies a radical of formula (a'),

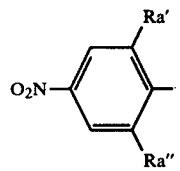

in which Ra' signifies hydrogen, halogen, preferably chlorine, nitro or cyano, and Ra" signifies hydrogen or halogen, preferably chlorine, a radical of formula (a")

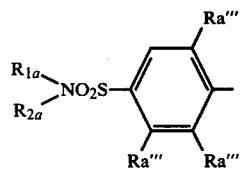

in which the Ra""'s, independently, signify hydrogen or halogen, preferably chlorine, and either $R_{1a}$ and $R_{2a}$, independently, signify an alkyl radical of 1 to 4 carbon atoms or are linked to form, together with the nitrogen atom, a morpholino radical;

a radical (d), in which $R_{23}$ signifies a phenyl radical or a 2-cyanophenyl radical; a radical (e), in which $R_{23}'$ signifies a phenyl radical; a radical (i), in which Ri signifies nitro; a radical (f), in which $R_{23}''$ signifies chlorine and $R_{23}'''$ signifies cyano; a radical (g), in which Rg and Rg' both signify bromine; a radical (h), in which Rh signifies nitro; a radical (j), in which Rj and Rj" each signify cyano and Rj' signifies methyl, or in which Rj signifies methoxycarbonyl, Rj' signifies methyl and Rj" signifies cyano.

K' preferably signifies a radical of formula (m), most preferably a radical of formula (m), in which $R_{18}$ signifies hydrogen or methyl.

$R_{16}$ most preferably signifies an ethyl radical.

T preferably signifies a radical

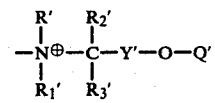

in which R', $R_1'$, $R_2'$, $R_3'$, Y' and Q' correspond to the preferred significances of R, $R_1$, $R_2$, $R_3$, Y and Q, as given above. As examples of other preferred compounds of formula Ia may be given the compounds of formula Iab,

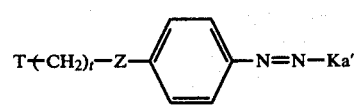

in which Ka' signifies a coupling component radical, Z signifies

or —SO$_2$—, preferably

t signifies 1 or 2, preferably 1, and

T is as defined above, preferably T', as defined above.

In the compounds of formula Iab, Ka' may, for example, be of the benzene, naphthalene, heterocyclic or aliphatic series. Suitable significances of Ka' will suggest themselves to those skilled in the art and, as will be appreciated, the particular significance of Ka' is of minor consequence in the invention. As examples of Ka' may be given the radicals of the formulae

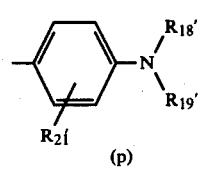
(p)

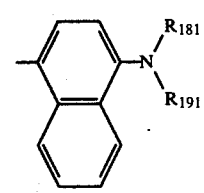
(q)

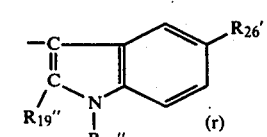
(r)

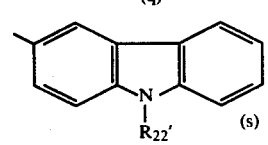
(s)

-continued

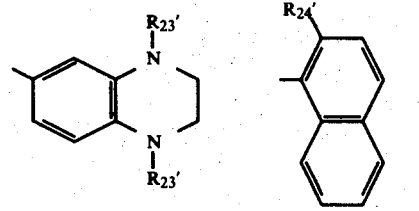

(t)                    (u)

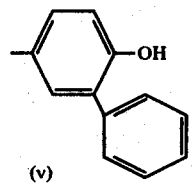    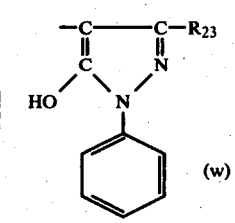

(v)                    (w)

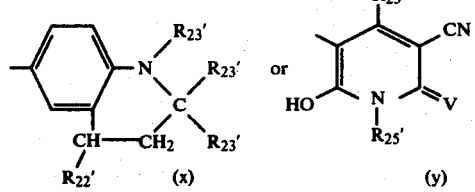

(x)                    (y)

in which $R_{18}'$ and $R_{19}'$, which may be the same or different, each signify hydrogen, or an alkyl
radical of 1 to 4 carbon atoms unsubstituted or substituted by $C_{1-4}$ alkoxycarbonyl, benzoyloxyl, phenoxy, halogen, preferably chlorine, hydroxy, cyano, $C_{1-4}$ alkoxy, $C_{1-4}$ alkylcarbonyloxy or N,N-di($C_{1-4}$) alkylamino, or one of $R_{18}'$ and $R_{19}'$ signifies phenyl or cyclohexyl, the other having a significance as defined above, or $R_{18}'$ and $R_{19}'$, together with the nitrogen atom to which they are attached, signify

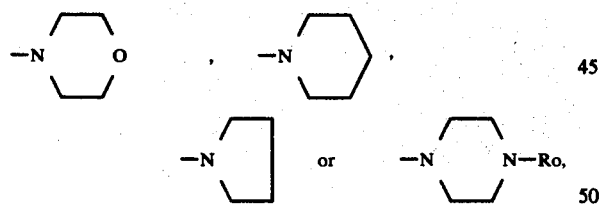

$R_{21}'$ signifies a hydrogen atom, a $C_{1-4}$ alkyl or alkoxy radical or a halogen atom, $R_{19}''$ signifies phenyl, $C_{1-4}$ alkyl, preferably methyl, unsubstituted or substituted by phenyl, e.g. benzyl, $R_{20}''$ signifies hydrogen, phenyl or $C_{1-4}$ alkyl, preferably methyl, $R_{22}'$ signifies $C_{1-4}$ alkyl, preferably methyl, the $R_{23}'$'s which may be the same or different, each signifies $C_{1-4}$ alkyl, preferably methyl, $R_{24}'$ signifies hydroxy, amino, or monophenylamino, $R_{25}'$ signifies hydrogen or an alkyl radical of 1 to 4 carbon atoms, unsubstituted or substituted by $C_{1-4}$ alkoxy, preferably methoxy, $R_{26}'$ signifies hydrogen or halogen, e.g. chlorine, or $C_{1-4}$ alkyl or alkoxy, preferably hydrogen, $R_{181}$ and $R_{191}$, independently, signify hydrogen or $C_{1-4}$ alkyl, or one of $R_{181}$ and $R_{191}$ signifies hydrogen or $C_{1-4}$ alkyl, and the other has one of the above significances of $R_{18}'$ or $R_{19}'$, and V signifies O or NH.

The preferred significances of Ka' are the above formulae (p), (r) and (y). In formula (p), above, $R_{21}'$ preferably signifies an alkyl radical of 1 to 4 carbon atoms, more preferably methyl, or a halogen atom, more preferably chlorine, $R_{18}'$ and $R_{19}'$ preferably signify hydrogen, $C_{1-4}$ alkyl, preferably ethyl, unsubstituted or substituted by cyano. In formula (r), $R_{19}''$ preferably signifies $C_{1-4}$ alkyl, e.g. methyl, or phenyl, $R_{20}''$ preferably signifies $C_{1-4}$ alkyl, preferably methyl, or hydrogen, and $R_{26}'$ preferably signifies hydrogen or halogen, preferably chlorine. In formula (y), $R_{23}'$ preferably signifies $C_{1-4}$ alkyl, preferably methyl, phenyl, $R_{25}'$ preferably signifies hydrogen, $C_{1-4}$ alkyl, unsubstituted or substituted by alkoxy, preferably methoxy; or phenyl, and V preferably signifies O.

As examples of further compounds of formula Ia may be given the compounds of formula Iac

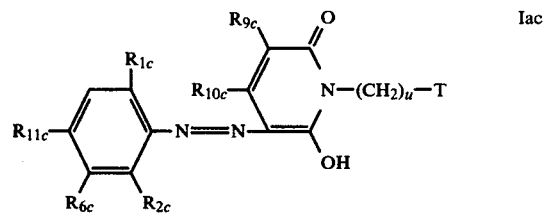

in which $R_{6c}$ signifies hydrogen, halogen, preferably chlorine, $C_{1-4}$ alkyl, preferably methyl, or $C_{1-4}$ alkoxy, preferably methoxy, $R_{1c}$ and $R_{2c}$, independently, signify hydrogen, alkyl of 1 to 4 carbon atoms, preferably methyl, halogen, preferably chlorine, nitro, cyano or $C_{1-4}$ alkoxy, preferably methoxy, $R_{11c}$ signifies hydrogen, phenoxy, halophenoxy, preferably 4-chlorophenoxy, $C_{1-4}$ alkoxy, preferably methoxy, $C_{1-4}$ alkyl, preferably methyl, $C_{1-4}$ alkoxycarbonyl, preferably ethoxycarbonyl, phenylazo or $C_{1-4}$ alkylphenylazo, preferably 4-methylphenylazo, with the proviso that (i) when $R_{11c}$ signifies phenylazo or ($C_{1-4}$ alkyl) phenylazo, $R_{2c}$ signifies hydrogen and $R_{1c}$ and $R_{6c}$, independently, signify hydrogen, $C_{1-4}$ alkyl, preferably methyl, $C_{1-4}$ alkoxy, preferably methoxy, more preferably $R_{1c}$ and $R_{6c}$ signifying hydrogen and (ii) the diazo component radical bears a maximum of 3 substituents, $R_{9c}$ signifies cyano, halogen, preferably chlorine, hydrogen or nitro, more preferably cyano, $R_{10c}$ signifies $C_{1-4}$ alkyl, preferably methyl, or phenyl, u signifies 2 or 3, preferably 3 and T is as defined above, T preferably signifying T', as defined above.

As still further examples of compounds of formula Ia may be given the compounds of formula Iad,

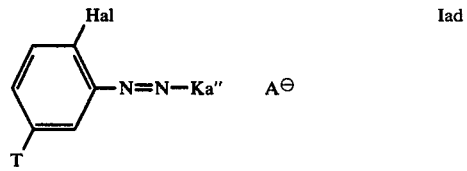

in which Hal signifies halogen, preferably chlorine,
Ka" signifies a radical (p), given above for Ka', and
T is as defined above.

In the compounds Iad, $R_{21}'$ (in radical [p]), preferably signifies methyl or chlorine, and $R_{18}'$ and $R_{19}'$, preferably signify, independently, hydrogen, ethyl or cyanoethyl. T preferably signifies T', above, more preferably $$-\overset{\oplus}{N}(CH_3)_2-C_2H_4-O-\text{phenyl}$$

As further examples of compounds provided by the invention may be given the dyes of the anthraquinone series of formula Ib,

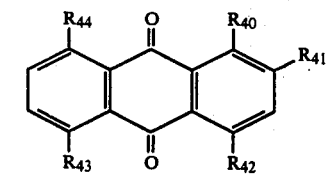

in which W signifies either a direct bond or a divalent bridging group,
$A^{\ominus}$ and T are as defined above, z signifies 1 or 2, and when z signifies 2, the W's and T's may be the same or different, the W(s) being bound to ring $Z_{10}$ or $Z_{11}$, and
rings $Z_{10}$ and $Z_{11}$ are optionally further substituted.

Among the preferred compounds of formula Ib are the compounds of formula Ib',

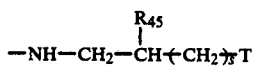

in which $R_{40}$ signifies $$-NH-CH_2-\overset{R_{45}}{\underset{|}{CH}}(CH_2)_s T$$

in which T is as defined above,
$R_{45}$ signifies hydrogen or hydroxy, preferably hydrogen,
s signifies 1 or 2,
or $R_{40}$ signifies hydroxy or $-NH-R_{46}$, in which $R_{46}$ signifies hydrogen; $C_{1-4}$ alkyl, preferably methyl; cyclohexyl; phenyl, unsubstituted or substituted by up to two substituents, selected from $C_{1-4}$ alkyl, preferably methyl, $C_{1-4}$ alkoxy, benzyloxy and halogen, preferably chlorine,
$R_{41}$ signifies $$-CONH\text{+}\overset{R_{45}}{\underset{|}{CH}}\text{+}_{x6} T$$

in which x6 signifies 2, 3 or 4, preferably 2 or 3,

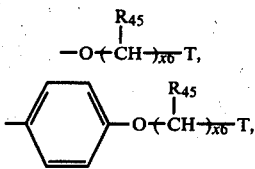

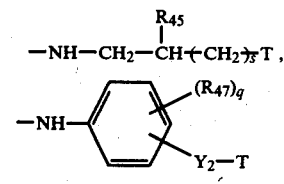

hydrogen, halogen, preferably bromine, cyano or
—CONH$_2$,
$R_{42}$ signifies

in which $R_{47}$ signifies halogen, preferably chlorine, or $C_{1-4}$ alkyl, preferably methyl,
q signifies 0, 1 or 2,
$Y_2$ signifies $$\text{+}\overset{R_{45}}{\underset{|}{CH}}\text{+}_{x2'} \text{ or } -O\text{+}\overset{R_{45}}{\underset{|}{CH}}\text{+}_{x2'}-$$

in which x2 signifies 1 or 2,
and x2' signifies 2 or 3, preferably 2; or —NH—$R_{46}$, in which $R_{46}$ is as defined above,
$R_{43}$ and $R_{44}$, which may be the same or different, each signify hydrogen, halogen, —NO$_2$, —NH$_2$ or —OH, a mono($C_{1-4}$) alkylamino or di-($C_{1-4}$) alkylamino radical, monophenylamino, a phenoxy radical or a monocyclohexylamino radical, most preferably both signify hydrogen,
with the proviso that the compounds contain one or two T groups.

The preferred compounds of formula Ib' contain only one T group.

Further examples of preferred compounds of formula Ib are the compounds of formula Iba,

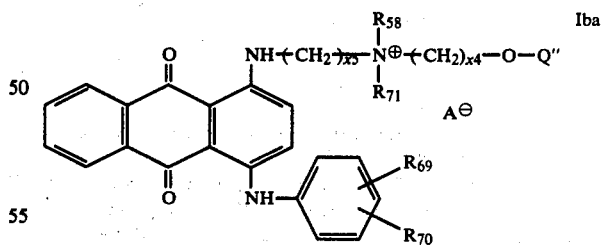

in which $R_{58}$ signifies a $C_{1-4}$ alkyl radical, preferably methyl or ethyl,
$R_{69}$ signifies hydrogen, $C_{1-4}$ alkyl, preferably methyl or ethyl, $C_{1-4}$ alkoxy, preferably methoxy or ethoxy, benzyloxy or halogen, preferably chlorine,
$R_{70}$ signifies hydrogen, $C_{1-4}$ alkyl, preferably methyl or ethyl, $C_{1-4}$ alkoxy, preferably methoxy or ethoxy, or halogen, preferably chlorine,
$R_{71}$ signifies methyl or ethyl,
Q" signifies an unsubstituted phenyl, biphenylyl, naphthyl or dibenzofuranyl radical or a phenyl radical substituted by halogen, preferably chlorine, cyano or nitro, x5 signifies 2 or 3, x4 signifies 2, 3 or 4, and A⊖ is as defined above, the compounds of formula Ibb,

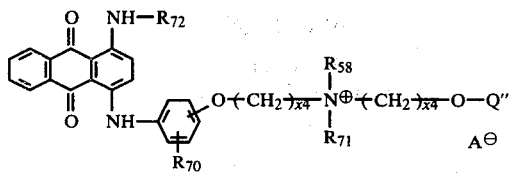

in which $R_{58}$, $R_{70}$, $R_{71}$, x4, Q″ and A⊖ are as defined above, and $R_{72}$ signifies hydrogen, $C_{1-4}$ alkyl, e.g. methyl, ethyl, propyl or butyl, or cyclohexyl, the compounds of formula Ibc,

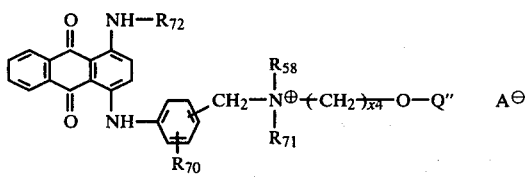

in which $R_{58}$, $R_{70}$, $R_{71}$, $R_{72}$, x4, Q″ and A⊖ are as defined above, the compounds of formula Ibd,

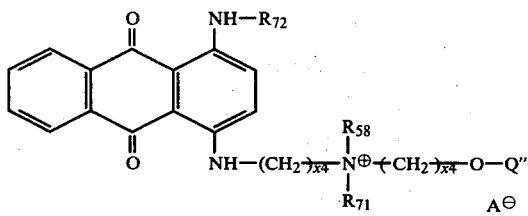

in which $R_{58}$, $R_{71}$, $R_{72}$, x4, Q″ and A⊖ are as defined above, and the compounds of formula Ibe,

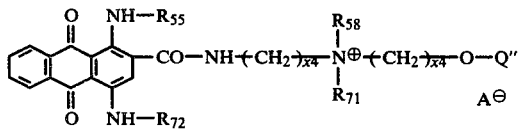

in which $R_{55}$ signifies hydrogen or methyl, and $R_{58}$, $R_{71}$, $R_{72}$, x4, Q″ and A⊖ are as defined above.

The compounds of the invention may be produced in conventional manner from available starting materials. For example, the compounds can be produced by reacting a compound of formula II,

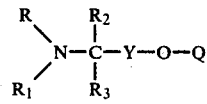

in which R, $R_1$, $R_2$, $R_3$ and Q are as defined above, with a dyestuff containing a leaving group such as the acid radical of an ester, e.g. a tosylate group, in conventional manner.

Where appropriate, the cleaving group may be an A⊖ yielding group or, if desired, the required A⊖ group may be introduced using conventional ion-exchange techniques.

Alternatively, for example, the compounds of the invention may be obtained by reacting a dyestuff containing the group

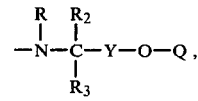

with quaternising agent of the formula $R_1$-A, in which $R_1$ is as defined above, and A is an A⊖ yielding group, in conventional manner.

The azo compounds of the invention may also be produced using conventional coupling techniques.

As examples of alkyl and alkoxy radicals of 1 to 4 carbon atoms, as used herein, may be given methyl, ethyl, n-propyl, isopropyl and n-butyl and the corresponding alkoxy radicals. Unless otherwise stated, the preferred such radicals are methyl, ethyl, methoxy and ethoxy, methyl and methoxy being most preferred. By the term halogen, as used herein, is meant chlorine, bromine and iodine; chlorine and bromine being preferred, chlorine being most preferred.

The compounds of formula I are useful as dyes. They may be converted into dyeing preparations, e.g. into stable, liquid or solid dyeing preparations, in conventional manner, e.g. by grinding or granulating or dissolving in conventional dyestuff solvents, if necessary with the addition of assistants such as stabilizers. Such preparations may be produced, for example, in accordance with French Patents 1,572,030 and 1,581,900.

The compounds of formula I may be used in the dyeing or printing of textile substrates, whether in fibre, yarn or fabric form, which consist of or comprise homopolymers or co-polymers of acrylonitrile or asymmetrical dicyanoethylene. The dyeing of such substrates may be carried out in conventional manner.

The compounds of formula I may also be used for dyeing or printing substrates of synthetic polyamide or synthetic polyester fibres, modified by the introduction of acid groups. Polyamides of this type are described in Belgian Patent 706,104 and polyester fibres of this type are described in U.S. Pat. No. 3,379,723. The dyeing of such substrates may be carried out in conventional manner. It is advantageous to dye in an aqueous, neutral or acid medium, at from 60° C. to the boil or at temperatures above 100° C. under pressure.

The dyeings obtained with the compounds of formula I are level, have stable light fastness as well as good wet fastness properties, e.g. to washing, perspiration, sublimation, pleating, decatizing, pressing, steam, water, sea water, dry cleaning, cross-dyeing and solvents. The dyes are well soluble in water, show good compatibility with salt, good stability to boiling, good pH stability and partly reserve fibres other than those on which they are dyeable. Further, they possess good power of build-up in combination with other basic dyes.

The compounds, which have good solubility in organic solvents, may also be used for the dyeing of natural or synthetic resins in the mass, being incorporated therein in conventional manner, e.g. by intimate admixture therein, for example by milling, optionally with the use of a solvent.

It has been found that mixtures of two or more of the compounds of the present invention or of one of the compounds of the present invention and other cationic dyes can be used with advantage.

The following Examples, in which parts and percentages are by weight and temperatures are in degrees centigrade, illustrate the invention.

EXAMPLE 1

17.2 Parts 1-amino-2-chloro-4-nitrobenzene are stirred into 30 parts concentrated hydrochloric acid, and then diluted with 200 parts ice and 100 parts water. Diazotization is accomplished according to a known method by the addition of a solution consisting of 7 parts sodium nitrite in 30 parts water. The resulting diazo solution is filtered and the excess sodium nitrite is decomposed with aminosulphonic acid. Finally the diazo solution is added dropwise to 37.8 parts of a coupling component of the formula

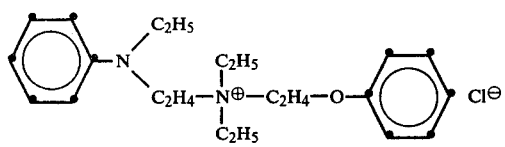

dissolved in 200 parts water. After coupling the pH of the solution is adjusted to a value from 4 to 5 by the addition of a 30% aqueous solution of sodium hydroxide and the resulting dye of the formula

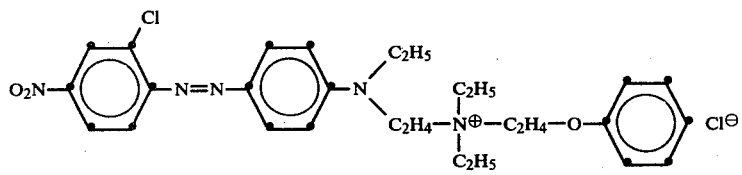

is filtered, washed with a 2% solution of sodium chloride, dried and ground. 49.5 Parts of a red-brown powder are obtained, which in an acid dyebath gives wet-fast and light-fast dyeings of a brownish-red shade on polyacrylonitrile fibres. Likewise, on acid-modified polyester and polyamide fibres the same fast brownish-red dyeings are obtained.

The coupling component are used above may be prepared in the following manner.

42.5 parts N,N-diethyl-N-2-phenoxyethylamine (obtained from the reaction of 1-phenoxy-2-chloroethane with diethylamine) are heated to 80° to 90° in a nitrogen atmosphere, together with 36.8 parts N-ethyl-N-2'-chloroethylaniline in 90 parts water and 10 parts ethyl alcohol. The reaction solution is stirred for 3 hours in this temperature range and the pH is adjusted to between 8 and 9 by the addition of sodium hydroxide. The solution is diluted with 50 parts water, cooled to a temperature between 40° and 50°, extracted twice each time with 100 parts of toluene and the toluene phase is separated. The coupling component is obtained in the form of a 40% aqueous solution which may be used directly for the preparation of the dye.

EXAMPLE 2

Instead of the coupling component in Example 1, 45.4 parts of the compound of the formula

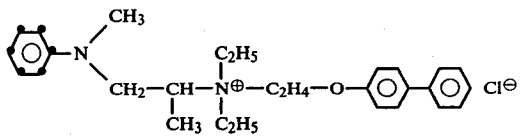

is employed, using a similar process to yield the dye of the formula

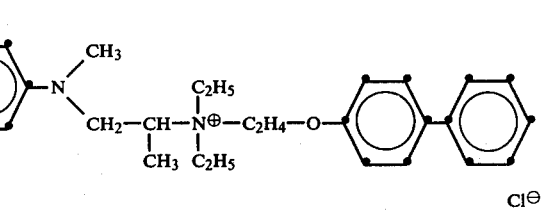

which, likewise, gives fast dyeings of a brownish-red shade on polyacrylonitrile and acid-modified polyester and polyamide fibres.

EXAMPLE 3

21 Parts 1-amino-2,6-dichloro-4-nitrobenzene are dissolved in 40 parts concentrated sulphuric acid at a temperature from 20° to 30° and is diazotized by the addition of a 40% solution of nitrosylsulfuric acid in concentrated sulphuric acid. The mixture is stirred into 100 parts water and 200 parts ice and is stirred for 2 hours after the completion of the diazotization. After the decomposition of the excess nitrosylsulphuric acid with aminosulphuric acid, the cold diazo solution is added dropwise to an aqueous solution consisting of 39.9 parts of the coupling component of the formula are used employing a similar process and the dye of the formula

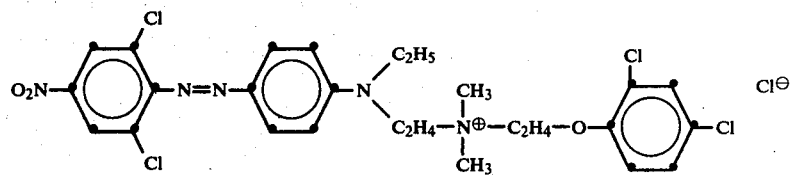

is obtained which gives fast yellow brown dyeings on polyacrylonitrile or acid-modified polyester or polyamide fibres.

EXAMPLE 5

In place of the coupling component of Example 4, 43.9 parts of the compound of the formula

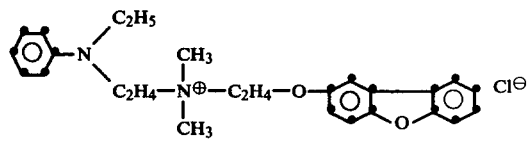

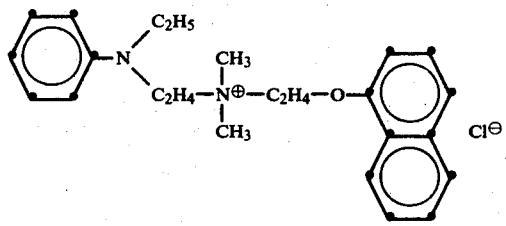

and 400 parts water, and the pH of the solution is adjusted to 3 by the addition of a caustic soda solution. After the addition of 40 parts sodium chloride the dye of the formula

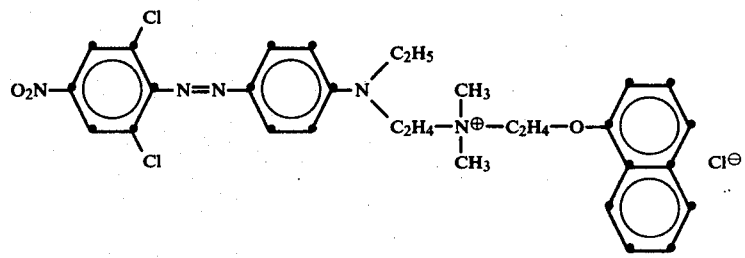

is precipitated out, filtered by suction, washed with a 2% sodium chloride solution, dried and ground, 51.9 Parts of a yellow-brown powder are obtained, which is used employing a similar process and the dye of the formula

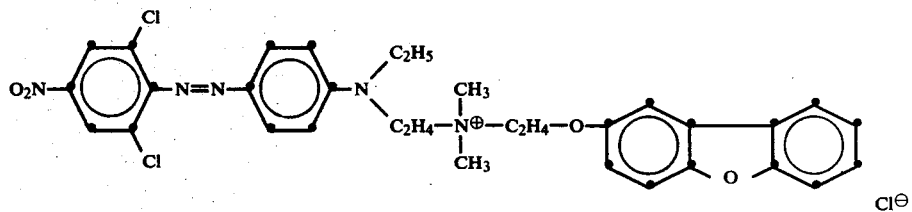

is obtained which likewise gives fast dyeings of a yellow brown shade on polyacrylonitrile and acid-modified polyester and polyamide fibres.

powder gives light-fast and wet-fast dyeings of a yellow brown shade on polyacrylonitrile fibres dyed in an acid bath. A similar fast dyeing of a yellow brown shade was obtained on acid-modified polyester and polyamide fibres.

EXAMPLE 4

In place of the coupling component of Example 3, 41.8 parts of the compound of the formula

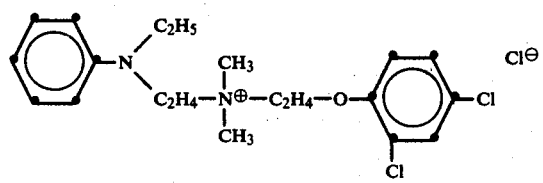

The structural composition of further dyes is shown in Table I. They may be produced in accordance with the procedure of Examples 1 to 5 and agree with the formula

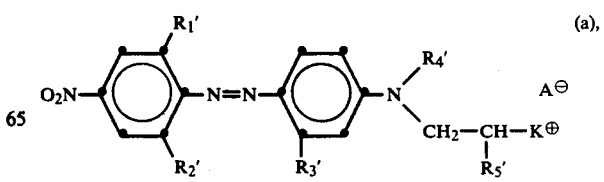

(a), in which $R_1'$ to $R_5'$ have the significances given in the columns. A further column I indicates the dye shade on polyacrylonitrile. The anion $A^{\ominus}$ may be any one of those named in the foregoing description. The symbol $K^{\oplus}$ may stand for any of the groups $K_1$ to $K_{46}$ shown in Table A. These groups in any single dye may be exchanged for any of the further groups given for $K_1$ to $K_{46}$.

Table A $K_1$ signifies the group 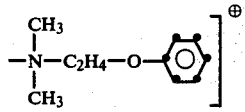

$K_2$ signifies the group 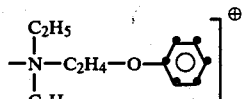

$K_3$ signifies the group 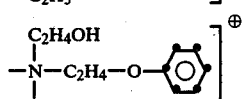

$K_4$ signifies the group 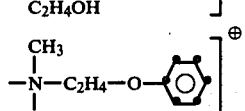

$K_5$ signifies the group 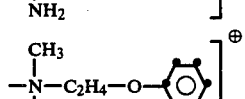

$K_6$ signifies the group 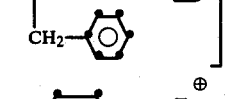

$K_7$ signifies the group 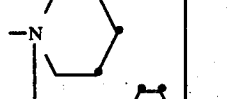

$K_8$ signifies the group 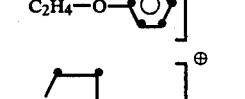

$K_9$ signifies the group 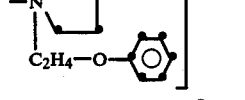

$K_{10}$ signifies the group 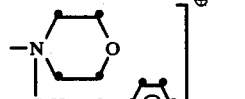

$K_{11}$ signifies the group 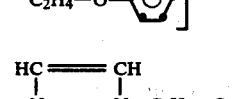

Table A-continued $K_{12}$ signifies the group 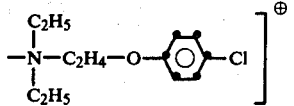

$K_{13}$ signifies the group 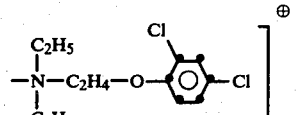

$K_{14}$ signifies the group 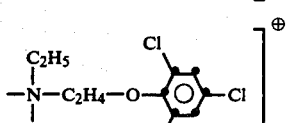

$K_{15}$ signifies the group 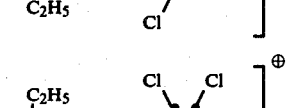

$K_{16}$ signifies the group 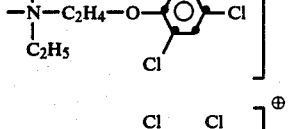

$K_{17}$ signifies the group 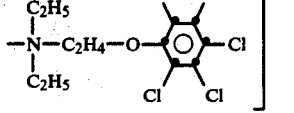

$K_{18}$ signifies the group 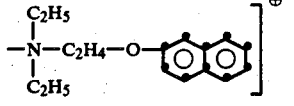

$K_{19}$ signifies the group 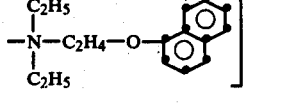

$K_{20}$ signifies the group 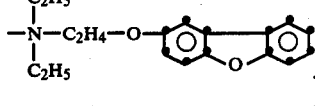

$K_{21}$ signifies the group 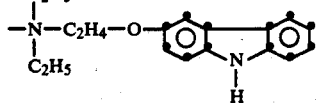

$K_{22}$ signifies the group 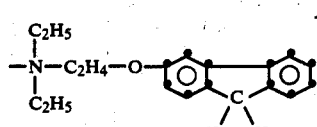

$K_{23}$ signifies the group 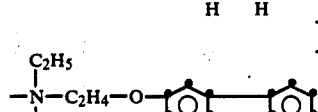

Table A-continued

K₂₄ signifies the group 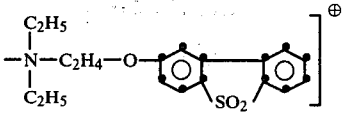

K₂₅ signifies the group 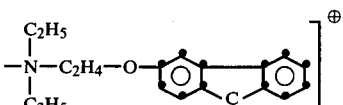

K₂₆ signifies the group 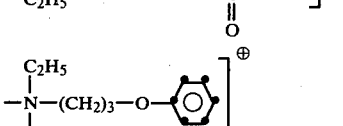

K₂₇ signifies the group 

K₂₈ signifies the group 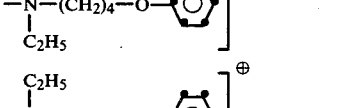

K₂₉ signifies the group 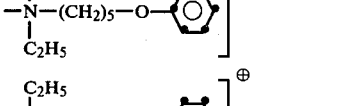

K₃₀ signifies the group 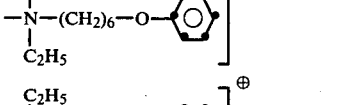

K₃₁ signifies the group 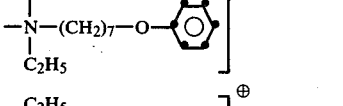

K₃₂ signifies the group 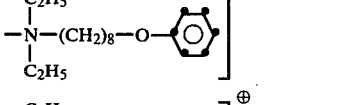

K₃₃ signifies the group 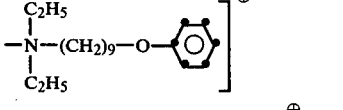

K₃₄ signifies the group 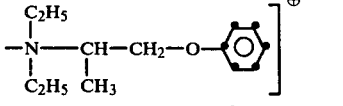

K₃₅ signifies the group 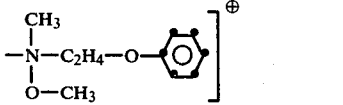

K₃₆ signifies the group 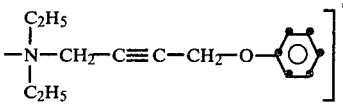

K₃₇ signifies the group 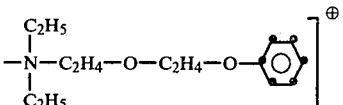

K₃₈ signifies the group 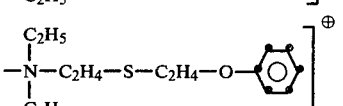

K₃₉ signifies the group 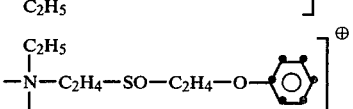

K₄₀ signifies the group 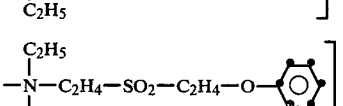

K₄₁ signifies the group 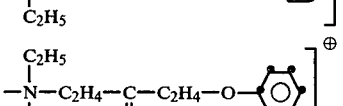

K₄₂ signifies the group 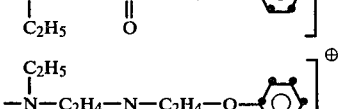

K₄₃ signifies the group 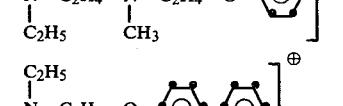

K₄₄ signifies the group 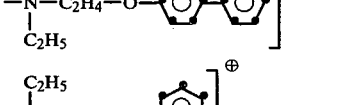

K₄₅ signifies the group 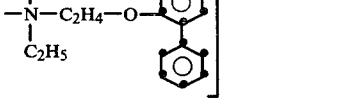

K₄₆ signifies the group 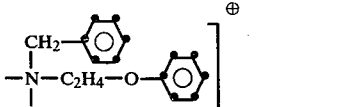

Table I

| Ex. | $R_1'$ | $R_2'$ | $R_3'$ | $R_5'$ | $R_4'$ | $K^\oplus$ | I |
|---|---|---|---|---|---|---|---|
| 6 | —Cl | H | H | H | —$C_2H_5$ | $K_1$ | brownish-red |
| 7 | " | H | H | H | " | $K_3$ | " |
| 8 | " | H | H | H | " | $K_4$ | " |
| 9 | " | H | H | H | " | $K_5$ | " |
| 10 | " | H | H | H | " | $K_6$ | " |
| 11 | " | H | H | H | " | $K_7$ | " |
| 12 | " | H | H | H | " | $K_8$ | " |
| 13 | " | H | H | H | " | $K_9$ | " |
| 14 | " | H | H | H | " | $K_{10}$ | " |
| 15 | " | H | H | H | " | $K_{11}$ | " |
| 16 | " | H | H | H | " | $K_{12}$ | " |

Table I-continued

| Ex. | R$_1'$ | R$_2'$ | R$_3'$ | R$_5'$ | R$_4'$ | K$^\oplus$ | I |
|---|---|---|---|---|---|---|---|
| 17 | " | H | H | H | " | K$_{13}$ | " |
| 18 | " | H | H | H | " | K$_{14}$ | " |
| 19 | " | H | H | H | " | K$_{15}$ | " |
| 20 | " | H | H | H | " | K$_{16}$ | " |
| 21 | " | H | H | H | " | K$_{17}$ | " |
| 22 | " | H | H | H | " | K$_{18}$ | " |
| 23 | " | H | H | H | " | K$_{19}$ | " |
| 24 | " | H | H | H | " | K$_{20}$ | " |
| 25 | " | H | H | H | " | K$_{21}$ | " |
| 26 | " | H | H | H | " | K$_{22}$ | " |
| 27 | " | H | H | H | " | K$_{23}$ | " |
| 28 | " | H | H | H | " | K$_{24}$ | " |
| 29 | " | H | H | H | " | K$_{25}$ | " |
| 30 | " | H | H | H | " | K$_{26}$ | " |
| 31 | " | H | H | H | " | K$_{27}$ | " |
| 32 | " | H | H | H | " | K$_{28}$ | " |
| 33 | " | H | H | H | " | K$_{29}$ | " |
| 34 | " | H | H | H | " | K$_{30}$ | " |
| 35 | " | H | H | H | " | K$_{31}$ | " |
| 36 | " | H | H | H | " | K$_{32}$ | " |
| 37 | " | H | H | H | " | K$_{33}$ | " |
| 38 | " | H | H | H | " | K$_{34}$ | " |
| 39 | " | H | H | H | " | K$_{35}$ | " |
| 40 | " | H | H | H | " | K$_{36}$ | " |
| 41 | " | H | H | H | " | K$_{37}$ | " |
| 42 | " | H | H | H | " | K$_{38}$ | " |
| 43 | " | H | H | H | " | K$_{39}$ | " |
| 44 | " | H | H | H | " | K$_{40}$ | " |
| 45 | " | H | H | H | " | K$_{41}$ | " |
| 46 | " | H | H | H | " | K$_{42}$ | " |
| 47 | " | H | H | H | " | K$_{43}$ | " |
| 48 | " | H | H | H | " | K$_{44}$ | " |
| 49 | " | H | H | —CH$_3$ | —CH$_3$ | K$_1$ | " |
| 50 | " | H | H | " | " | K$_2$ | " |
| 51 | " | H | H | " | " | K$_{13}$ | " |
| 52 | " | H | —CH$_3$ | " | " | K$_{17}$ | " |
| 53 | " | H | —OCH$_3$ | " | " | K$_{18}$ | " |
| 54 | " | H | —Cl | " | " | K$_{44}$ | yellowish-orange |
| 55 | " | —Cl | H | H | —C$_2$H$_5$ | K$_1$ | yellowish-brown |
| 56 | " | " | H | H | " | K$_2$ | " |
| 57 | " | " | H | H | " | K$_{13}$ | " |
| 58 | " | " | H | H | " | K$_{17}$ | " |
| 59 | " | " | H | H | " | K$_{18}$ | " |
| 60 | " | " | H | H | " | K$_{19}$ | " |
| 61 | " | " | H | H | " | K$_{35}$ | " |
| 62 | " | " | H | H | " | K$_{43}$ | " |
| 63 | " | " | H | H | " | K$_{44}$ | " |
| 64 | " | " | H | H | " | K$_{12}$ | " |
| 65 | " | " | H | H | " | K$_{14}$ | " |
| 66 | " | " | H | H | " | K$_{15}$ | " |
| 67 | " | " | H | H | " | K$_{16}$ | " |
| 68 | " | " | H | H | " | K$_{36}$ | " |
| 69 | " | " | H | H | " | K$_{37}$ | " |
| 70 | " | " | —CH$_3$ | H | " | K$_1$ | " |
| 71 | " | " | " | H | " | K$_2$ | " |
| 72 | —CN | H | H | H | " | K$_1$ | rubine |
| 73 | " | H | H | H | " | K$_2$ | " |
| 74 | " | H | H | H | " | K$_{13}$ | " |
| 75 | " | H | H | H | " | K$_{17}$ | " |
| 76 | " | H | H | H | " | K$_{18}$ | " |
| 77 | " | H | H | H | " | K$_{19}$ | " |
| 78 | " | H | H | H | " | K$_{35}$ | " |
| 79 | " | H | H | H | " | K$_{43}$ | " |
| 80 | " | H | H | H | " | K$_{44}$ | " |
| 81 | " | H | H | —CH$_3$ | —CH$_3$ | K$_2$ | " |
| 82 | —NO$_2$ | —Br | —CH$_3$ | H | —C$_2$H$_5$ | K$_1$ | violet |
| 83 | " | " | " | H | " | K$_2$ | " |
| 84 | " | " | " | H | " | K$_{13}$ | " |
| 85 | " | " | " | H | " | K$_{17}$ | " |
| 86 | " | " | " | H | " | K$_{18}$ | " |
| 87 | " | " | " | H | " | K$_{19}$ | " |
| 88 | " | " | " | H | " | K$_{35}$ | " |
| 89 | " | " | " | H | " | K$_{43}$ | " |
| 90 | " | " | " | H | " | K$_{44}$ | " |
| 91 | " | " | " | —CH$_3$ | " | K$_2$ | " |
| 92 | " | " | H | H | " | K$_2$ | reddish-violet |
| 93 | " | —Cl | —CH$_3$ | H | " | K$_2$ | violet |
| 94 | —CF$_3$ | H | H | H | " | K$_2$ | rubine |
| 95 | —SO$_2$CH$_3$ | H | H | H | " | K$_2$ | " |
| 96 | —CH$_3$ | H | H | H | " | K$_2$ | brownish-red |
| 97 | —OCH$_3$ | H | H | H | " | K$_2$ | " |

Table I-continued

| Ex. | R₁' | R₂' | R₃' | R₅' | R₄' | K⊕ | I |
|---|---|---|---|---|---|---|---|
| 98 | —CN | —CN | —CH₃ | H | " | K₂ | bluish-violet |
| 99 | —NO₂ | —NO₂ | " | H | " | K₂ | " |
| 100 | —Cl | H | H | H | —C₄H₉ | K₂ | brownish-red |
| 101 | " | H | H | H | —C₂H₄CN | K₂ | " |
| 102 | " | H | H | H | —C₂H₄—COO—C₂H₅ | K₂ | " |
| 103 | | | | | | | orange |
| 104 | | | | | | | red |
| 105 | | | | | | | bluish-violet |
| 106 | | | | | | | reddish-blue |
| 107 | | | | | | | reddish-violet |

The structural composition of further dyes is shown in Table II. They can be produced in accordance with the procedure of Examples 3 to 5 and agree with the formula

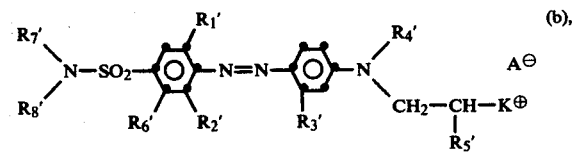

(b), in which $R_1'$ to $R_8'$ and $K^\oplus$ have the significances as shown in the columns of the Table A. A further column I shows the dye-shade on polyacrylonitrile. The anion $A^\ominus$ may be any one of those named in the foregoing description.

Table II

| Ex. | R₁' | R₂' | R₃' | R₅' | R₆' | R₇' | R₈' | R₄' | K⊕ | I |
|---|---|---|---|---|---|---|---|---|---|---|
| 108 | —Cl | —Cl | H | H | H | —CH₃ | —CH₃ | —C₂H₅ | K₁ | golden-yellow |
| 109 | " | " | H | H | H | " | " | " | K₂ | " |
| 110 | " | " | H | H | H | " | " | " | K₁₂ | " |
| 111 | " | " | H | H | H | " | " | " | K₁₃ | " |
| 112 | " | " | H | H | H | " | " | " | K₁₄ | " |
| 113 | " | " | H | H | H | " | " | " | K₁₅ | " |
| 114 | " | " | H | H | H | " | " | " | K₁₆ | " |
| 115 | " | " | H | H | H | " | " | " | K₁₇ | " |
| 116 | " | " | H | H | H | " | " | " | K₁₈ | " |
| 117 | " | " | H | H | H | " | " | " | K₁₉ | " |
| 118 | " | " | H | H | H | " | " | " | K₃₅ | " |
| 119 | " | " | H | H | H | " | " | " | K₃₆ | " |
| 120 | " | " | H | H | H | " | " | " | K₃₇ | " |
| 121 | " | " | H | H | H | " | " | " | K₄₃ | " |
| 122 | " | " | H | H | H | " | " | " | K₄₄ | " |
| 123 | " | " | —CH₃ | H | H | " | " | " | K₂ | reddish-yellow |
| 124 | " | " | H | —CH₃ | H | " | " | —CH₃ | K₂ | reddish-yellow |
| 125 | " | " | H | H | H | —(CH₂)₅ | | —C₂H₅ | K₂ | golden-yellow |

Table II-continued

| Ex. | R$_1'$ | R$_2'$ | R$_3'$ | R$_5'$ | R$_6'$ | R$_7'$ | R$_8'$ | R$_4'$ | K$^\oplus$ | I |
|---|---|---|---|---|---|---|---|---|---|---|
| 126 | " | " | H | H | H | —C$_2$H$_4$—O—C$_2$H$_4$— | | " | K$_2$ | " |
| 127 | " | " | H | H | H | —C$_4$H$_9$ | —C$_4$H$_9$ | " | K$_2$ | " |
| 128 | " | H | H | H | —Cl | —CH$_3$ | —CH$_3$ | " | K$_1$ | orange |
| 129 | " | H | H | H | " | " | " | " | K$_2$ | " |
| 130 | " | H | H | H | " | " | " | " | K$_{12}$ | " |
| 131 | " | H | H | H | " | " | " | " | K$_{13}$ | " |
| 132 | " | H | H | H | " | " | " | " | K$_{14}$ | " |
| 133 | " | H | H | H | " | " | " | " | K$_{15}$ | " |
| 134 | " | H | H | H | " | " | " | " | K$_{16}$ | " |
| 135 | " | H | H | H | " | " | " | " | K$_{17}$ | " |
| 136 | " | H | H | H | " | " | " | " | K$_{18}$ | " |
| 137 | " | H | H | H | " | " | " | " | K$_{19}$ | " |
| 138 | " | H | H | H | " | " | " | " | K$_{20}$ | " |
| 139 | " | H | H | H | " | " | " | " | K$_{35}$ | orange |
| 140 | " | H | H | H | " | " | " | " | K$_{36}$ | " |
| 141 | " | H | H | H | " | " | " | " | K$_{37}$ | " |
| 142 | " | H | H | H | " | " | " | " | K$_{43}$ | " |
| 143 | " | H | H | H | " | " | " | " | K$_{44}$ | " |
| 144 | " | H | H | —CH$_3$ | " | " | " | —CH$_3$ | K$_2$ | " |
| 145 | " | H | H | H | " | —C$_2$H$_4$—O—C$_2$H$_4$— | | —C$_2$H$_5$ | K$_2$ | " |
| 146 | " | H | H | H | " | —(CH$_2$)$_5$— | | " | K$_2$ | " |

EXAMPLE 147

17.8 Parts 4-amino-ω-dimethylaminoacetophenone (prepared by the reaction between 4-acetamido ω-chloroacetophenone with dimethylamine and saponification of the acetamino group) are diazotized at 0° C. employing conventional methods. The pH is adjusted to 8.0 by the addition of sodium carbonate and over the period of one hour a solution of 16.3 parts N,N-diethyl-m-toluidine, dissolved in 150 parts water and 50 parts glacial acetic acid, is added dropwise. After completion of the coupling reaction, the dye is salted out with sodium chloride, filtered, washed with a dilute brine solution, dried and ground. 17 Parts of the dye so obtained are dissolved in 75 parts isopropanol and 75 parts ethylmethylketone and over the period of 1 hour are mixed with 20.3 parts 1-phenoxy-4-chlorobut-2,3-ene. After two more hours at boiling temperature, the mixture is cooled to room temperature, the dye, after the addition of ether or dioxane, is filtered and washed with acetone and agrees with the formula

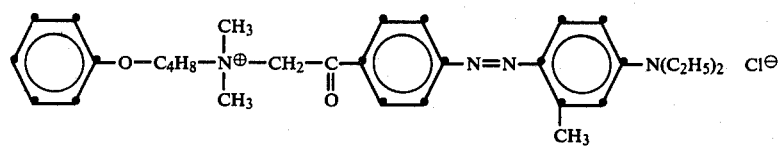

Fast red dyeings are obtained on polyacrylonitrile as well as on acid-modified polyester on polyamide fibres.

EXAMPLE 148

In place of the 1-phenoxy-4-chlorobut-2,3-ene used in Example 147, 18.6 parts of the compound of the formula

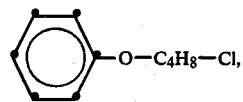

(obtained by condensing sodium phenoxide with 1,4-dichlorobutane in the presence of sodium iodide), is employed using the procedure as described in Example 147 and the dye of the formula is obtained which likewise gives fast red dyeings on polyacrylontrile as well as on acid-modified polyester and polyamide fibres.

The structural composition of further dyes is shown in Table III. The dyes can be produced in accordance with the procedure of Examples 147 and 148 and agree with the formula (c),

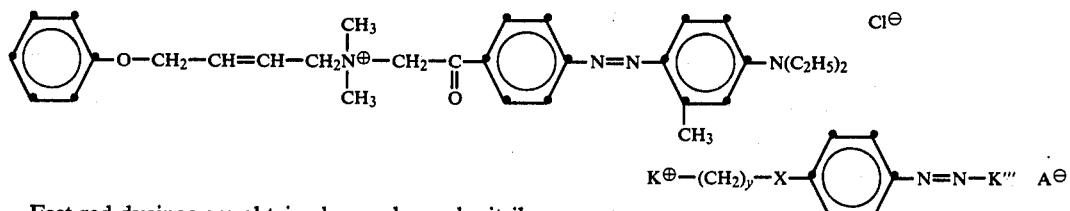

in which R$^\oplus$, K''', X and Y have the significances as shown in the columns. A further column I indicates the shade of dyeing obtained on polyacrylonitrile. The anion A$^\ominus$ may be any one of those named in the foregoing description.

Table III

| Ex. | X | Y | K⊖ | K''' | I |
|---|---|---|---|---|---|
| 149 | −CO− | 1 | $K_1$ | 4-[N(C$_2$H$_5$)], 3-CH$_3$ phenyl | red |
| 150 | " | 1 | $K_2$ | " | " |
| 151 | " | 1 | $K_{13}$ | " | " |
| 152 | " | 1 | $K_{17}$ | " | " |
| 153 | " | 1 | $K_{18}$ | " | " |
| 154 | " | 1 | $K_{19}$ | " | " |
| 155 | " | 1 | $K_{35}$ | " | " |
| 156 | " | 1 | $K_{43}$ | " | " |
| 157 | " | 1 | $K_{44}$ | " | " |
| 158 | −SO$_2$− | 1 | $K_2$ | " | " |
| 159 | −CO− | 2 | $K_2$ | " | orange |
| 160 | " | 1 | $K_1$ | 4-[NH−C$_2$H$_4$−CN], 3-Cl phenyl | reddish-yellow |
| 161 | " | 1 | $K_2$ | " | " |
| 162 | " | 1 | $K_1$ | 2,3-dimethylindole (NH) | " |
| 163 | " | 1 | $K_2$ | " | " |
| 164 | " | 1 | $K_{13}$ | " | " |
| 165 | " | 1 | $K_{17}$ | " | " |
| 166 | " | 1 | $K_{18}$ | " | " |
| 167 | " | 1 | $K_{19}$ | " | " |
| 168 | " | 1 | $K_{35}$ | " | " |
| 169 | " | 1 | $K_{43}$ | " | " |
| 170 | " | 1 | $K_{44}$ | " | " |
| 171 | " | 1 | $K_1$ | 1,2,3-trimethylindole | " |
| 172 | " | 1 | $K_2$ | " | " |
| 172a | " | 1 | $K_2$ | 3-methyl-2-phenylindole (NH) | " |
| 173 | " | 1 | $K_2$ | 5-chloro-3-methyl-2-phenylindole (NH) | " |
| 174 | " | 1 | $K_1$ | 4-CH$_3$, 3-CN, 6-OH, 2-oxo-1H-pyridine | yellow |
| 175 | " | 1 | $K_2$ | " | " |
| 176 | " | 1 | $K_{13}$ | " | " |
| 177 | " | 1 | $K_{17}$ | " | " |
| 178 | " | 1 | $K_{18}$ | " | " |
| 179 | " | 1 | $K_{19}$ | " | " |
| 180 | " | 1 | $K_{35}$ | " | " |
| 181 | " | 1 | $K_{43}$ | " | " |
| 182 | " | 1 | $K_{44}$ | " | " |
| 183 | " | 1 | $K_{12}$ | " | " |

Table III-continued

| Ex. | X | Y | K⊖ | K''' | I |
|---|---|---|---|---|---|
| 184 | " | 1 | K₁ | (structure: 4-methyl-3-cyano-6-hydroxy-1-methyl-pyridin-2-one) | " |
| 185 | " | 1 | K₂ | " | " |
| 186 | " | 1 | K₁ | (structure: 4-methyl-3-cyano-6-hydroxy-1-(3-methoxypropyl)-pyridin-2-one) | " |
| 187 | " | 1 | K₂ | " | " |
| 188 | " | 1 | K₂ | (structure: phenyl-substituted pyridinone with CN, N—H, OH, CH₃) | " |
| 189 | " | 1 | K₂ | (structure: 3-cyano-4-methyl-6-hydroxy-1-(phenylamino)-pyridin-2-one) | " |

EXAMPLE 190

25.6 parts of 4-amino-4'-chloro-diphenylether-chlorohydrate are dissolved in 300 parts water and are diazotized, after the addition of 18 parts of 30% hydrochloric acid with 6.9 parts sodium nitrite, according to conventional methods. This diazo solution is added to 24.7 parts of the coupling component of the formula

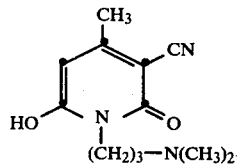

dissolved in 200 parts 2% hydrochloric acid. After completion of the coupling, the dye of the formula

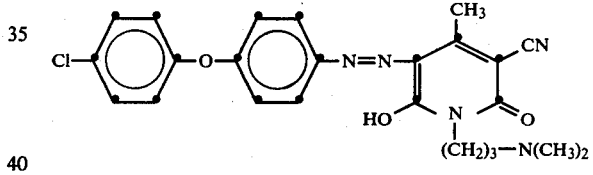

is salted out with sodium chloride at 60°, filtered and dried. 15 Parts of the dye so obtained are diluted with 75 parts isopropyl alcohol and 75 parts ethylmethylketone, mixed with 9.0 parts 2-phenoxy-1-chloroethane and the mixture is heated for 3 hours. After cooling, the quaternated dye of the formula

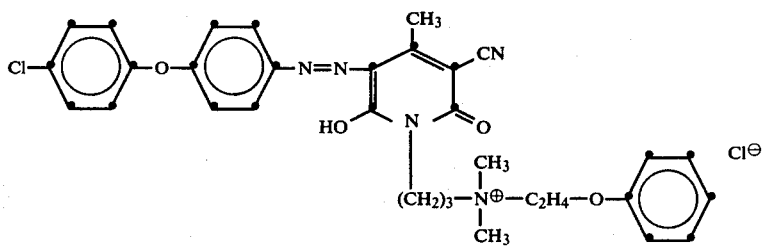

is precipitated out with ether, dioxane or acetone. After filtering, drying and grinding a dye is obtained which gives light-fast and wet-fast dyeings of a reddish-yellow shade on polycrylonitrile, acid-modified polyesters and polyamide fibres.

The coupling component may be prepared by condensing cyanoacetic acid-3-dimethylamino-n-propylamide with ethyl acetate.

EXAMPLE 191

In place of the 2-phenoxy-1-chloroethane quaternating agent of Example 190, the compound of the formula

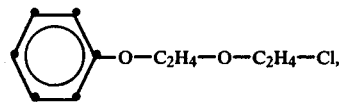

is used, employing the same method, to obtain the dye of the formula

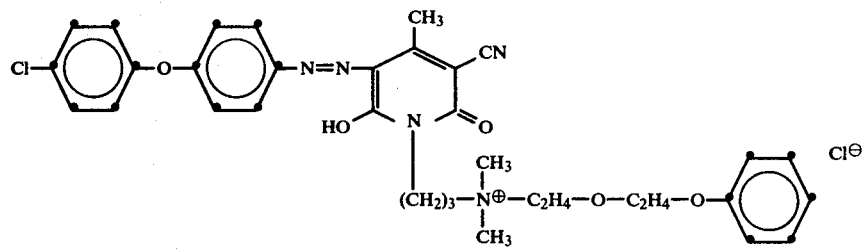

which dye likewise gives fast reddish-yellow dyeings on polyacrylonitrile as well as on acid-modified polyester and polyamide fibres.

The structural composition of further dyes is shown in Table IV. They may be prepared according to the procedure of Examples 190 and 191 and agree with the formula

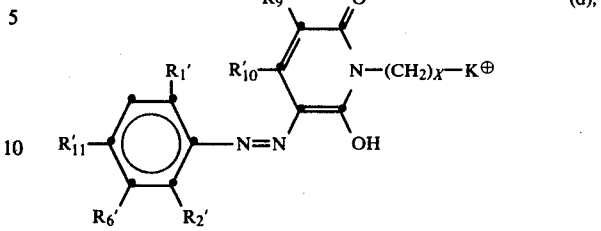

in which $R_1'$, $R_2'$, $R_6'$, $R_9'$ to $R_{11}'$ and $K^\oplus$ have the significances as shown in the columns. A further column I indicates the dye shade on polyacrylonitrile. The anion $A^\ominus$ may be any one of those named in the foregoing description.

Table IV

| Ex. | $R_1'$ | $R_2'$ | $R_6'$ | $R_9'$ | $R_{10}'$ | X | $K^\oplus$ | $R_{11}'$ | I |
|-----|--------|--------|--------|--------|-----------|---|------------|-----------|---|
| 192 | H | H | H | —CN | —CH$_3$ | 3 | K$_1$ | Cl—⌬—O— | yellow |
| 193 | H | H | H | " | " | 3 | K$_2$ | " | " |
| 194 | H | H | H | " | " | 3 | K$_{12}$ | " | " |
| 195 | H | H | H | " | " | 3 | K$_{13}$ | " | " |
| 196 | H | H | H | " | " | 3 | K$_{14}$ | " | " |
| 197 | H | H | H | " | " | 3 | K$_{15}$ | " | " |
| 198 | H | H | H | " | " | 3 | K$_{16}$ | " | " |
| 199 | H | H | H | " | " | 3 | K$_{17}$ | " | " |
| 200 | H | H | H | " | " | 3 | K$_{18}$ | " | " |
| 201 | H | H | H | " | " | 3 | K$_{19}$ | " | " |
| 202 | H | H | H | " | " | 3 | K$_{35}$ | " | " |
| 203 | H | H | H | " | " | 3 | K$_{36}$ | " | " |
| 204 | H | H | H | " | " | 3 | K$_{43}$ | " | " |
| 205 | H | H | H | " | " | 3 | K$_{44}$ | " | " |
| 206 | —Cl | H | —Cl | " | " | 3 | K$_2$ | H | " |
| 207 | " | H | " | " | " | 3 | K$_{17}$ | H | " |
| 208 | " | H | " | " | " | 3 | K$_{19}$ | H | " |
| 209 | " | H | " | " | " | 3 | K$_{43}$ | H | " |
| 210 | H | H | H | " | " | 3 | K$_2$ | ⌬—N=N— | golden yellow |
| 211 | H | H | H | " | " | 3 | K$_{17}$ | " | " |
| 212 | H | H | H | " | " | 3 | K$_{43}$ | " | " |
| 213 | —CH$_3$ | H | H | " | " | 3 | K$_2$ | CH$_3$-⌬-N=N— | reddish-yellow |
| 214 | H | H | —Cl | " | " | 3 | K$_2$ | CH$_3$O— | " |
| 215 | H | H | H | " | " | 3 | K$_2$ | H | greenish-yellow |
| 216 | H | H | Cl | " | " | 3 | K$_2$ | —CH$_3$ | yellow |
| 217 | H | —Cl | " | " | " | 3 | K$_2$ | H | greenish-yellow |
| 218 | H | H | " | " | " | 3 | K$_2$ | H | " |
| 219 | H | H | " | " | " | 3 | K$_2$ | —COOC$_2$H$_5$ | " |

Table IV-continued

| Ex. | R$_1'$ | R$_2'$ | R$_6'$ | R$_9'$ | R$_{10}'$ | X | K$^\oplus$ | R$_{11}'$ | I |
|---|---|---|---|---|---|---|---|---|---|
| 220 | H | H | H | " | " | 2 | K$_2$ | 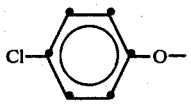 | yellow |
| 221 | H | H | H | H | " | 3 | K$_2$ | " | " |
| 222 | H | H | H | —Cl | " | 3 | K$_2$ | " | " |
| 223 | H | H | H | —NO$_2$ | " | 3 | K$_2$ | " | " |
| 224 | H | H | H | —CN | " | 3 | K$_2$ | " | " |

EXAMPLE 225

40 Parts nitrosylsulphuric acid with a nitric acid strength of 6.4% is stirred with a mixture of 50 parts acetic acid and 50 parts phosphoric acid under cooling at a temperature from −5° to 0°. 17.7 Parts of 5-amino-3-phenyl-1,2,4-thiadiazole are added to the reaction mixture and the further 60 parts of the mixture of 50 parts acetic acid and 50 parts phosphoric acid is added thereto and stirring is effected at the same temperature for 2½ hours.

After clarification the clear yellow diazo solution is added dropwise to an aqueous solution consisting of 39.1 parts of the coupling component of the formula

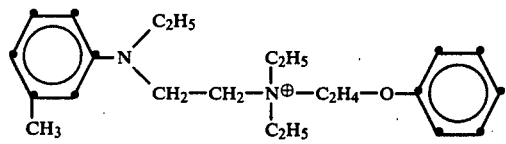

in 300 parts water including 2 parts sodium acetate and 5 parts aminosulphonic acid. The mixture is stirred for 1 hour and the pH of the solution is adjusted to a value from 4 to 5 by the addition of sodium hydroxide; then, with the addition of 30 parts sodium chloride, the dye of the formula

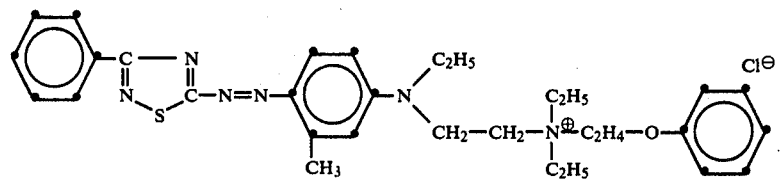

is salted out. After filtering, washing with a dilute brine solution, drying and grinding, 51 parts of a red powder is obtained which fast bluish-red dyeings on polyacrylonitrile and acid-modified polyester and polyamide fibres.

EXAMPLE 226

In place of the coupling component used in Example 225, 39.9 parts of the compound of the formula

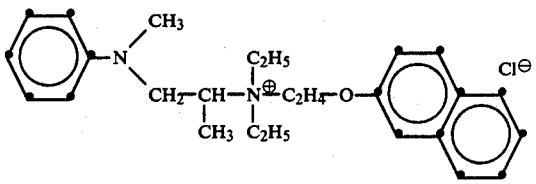

is used to obtain a similar dye of the formula

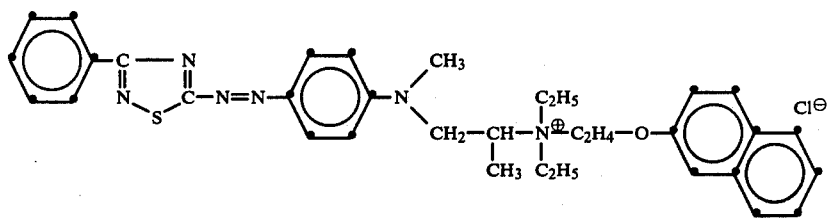

which on polyacrylonitrile as well as on acid-modified polyamide and polyester fibres gives fast dyeings of a yellowish red shade.

The structural composition of further dyes is shown in Table V. They can be in accordance with the process of Examples 225 and 226 and correspond with the formula

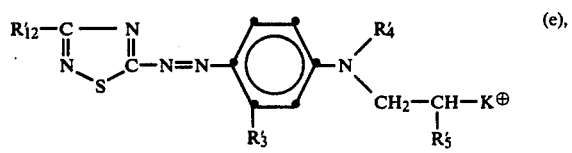

(e)

in which $R_3'$ to $R_5'$, $R_{12}'$ and $K^\oplus$ have the significances as shown in the columns. A further column I indicates the dye-shade on polyacrylonitrile. The anion $A^\ominus$ may be any one of those named in the foregoing description.

Table V

| Ex. | $R_3'$ | $R_5'$ | $R_{12}'$ | $K^\oplus$ | $R_4$ | I |
|---|---|---|---|---|---|---|
| 227 | H | H | 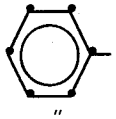 | $K_1$ | —$C_2H_5$ | yellowish-red |
| 228 | H | H | " | $K_2$ | " | yellowish-red |
| 229 | H | H | " | $K_{12}$ | " | yellowish-red |
| 230 | H | H | " | $K_{13}$ | " | yellowish-red |
| 231 | H | H | " | $K_{14}$ | " | yellowish-red |
| 232 | H | H | " | $K_{15}$ | " | yellowish-red |
| 233 | H | H | " | $K_{16}$ | " | yellowish-red |
| 234 | H | H | " | $K_{17}$ | " | yellowish-red |
| 235 | H | H | " | $K_{18}$ | " | yellowish-red |
| 236 | H | H | " | $K_{19}$ | " | yellowish-red |
| 237 | H | H | " | $K_{35}$ | " | yellowish-red |
| 238 | H | H | " | $K_{36}$ | " | yellowish-red |
| 239 | H | H | " | $K_{37}$ | " | yellowish-red |
| 240 | H | H | " | $K_{43}$ | " | yellowish-red |
| 241 | H | H | " | $K_{44}$ | " | yellowish-red |
| 242 | H | —$CH_3$ | " | $K_1$ | —$CH_3$ | yellowish-red |
| 243 | H | " | " | $K_2$ | " | yellowish-red |
| 244 | H | " | " | $K_{12}$ | " | yellowish-Red |
| 245 | H | " | " | $K_{13}$ | " | yellowish-red |
| 246 | H | " | " | $K_{14}$ | " | yellowish-red |
| 247 | H | " | " | $K_{15}$ | " | yellowish-red |
| 248 | H | " | " | $K_{16}$ | " | yellowish-red |
| 249 | H | " | " | $K_{17}$ | " | yellowish-red |
| 250 | H | " | " | $K_{18}$ | " | yellowish-red |
| 251 | H | " | " | $K_{19}$ | " | yellowish-red |
| 252 | H | " | " | $K_{35}$ | " | yellowish-red |
| 253 | H | " | " | $K_{36}$ | " | yellowish-red |
| 254 | H | " | " | $K_{37}$ | " | yellowish-red |
| 255 | H | " | " | $K_{43}$ | " | yellowish-red |
| 256 | H | " | " | $K_{44}$ | " | yellowish-red |
| 257 | —$CH_3$ | H | " | $K_1$ | —$C_2H_5$ | bluish-red |
| 258 | " | H | " | $K_3$ | " | bluish-red |
| 259 | " | H | " | $K_{12}$ | " | bluish-red |
| 260 | " | H | " | $K_{13}$ | " | bluish-red |
| 261 | " | H | " | $K_{14}$ | " | bluish-red |
| 262 | " | H | " | $K_{15}$ | " | bluish red |
| 263 | " | H | " | $K_{16}$ | " | bluish-red |

Table V-continued

| Ex. | R₃ | R₅ | R'₁₂ | K⊕ | R₄ | I |
|---|---|---|---|---|---|---|
| 264 | " | H | " | K₁₇ | " | bluish-red |
| 265 | " | H | " | K₁₈ | " | bluish-red |
| 266 | " | H | " | K₁₉ | " | bluish-red |
| 267 | " | H | " | K₃₅ | " | bluish-red |
| 268 | " | H | " | K₃₆ | " | bluish-red |
| 269 | " | H | " | K₃₇ | " | bluish-red |
| 270 | " | H | " | K₄₃ | " | bluish-red |
| 271 | " | H | " | K₄₄ | " | bluish-red |
| 272 | " | H | 2-methylphenyl | K₂ | " | bluish-red |
| 273 | " | H | 3-methylphenyl | K₂ | " | bluish-red |
| 274 | " | H | 2-cyanophenyl | K₂ | " | bluish-red |
| 275 | " | H | 4-nitrophenyl | K₂ | " | bluish-red |
| 276 | " | H | CH₃SO₂— | K₂ | " | bluish-red |
| 277 | " | H | CH₃SO— | K₂ | " | bluish-red |
| 278 | " | H | CH₃—S— | K₂ | " | bluish-red |
| 279 | " | H | Cl— | K₂ | " | red |
| 280 | " | H | CH₃— | K₂ | " | red |
| 281 | H | —CH₃ | 2-cyanophenyl | K₂ | —CH₃ | yellowish-red |
| 282 | H | " | phenyl | K₂ | —C₄H₉ | yellowish-red |
| 283 | H | " | " | K₂ | —C₂H₄CN | orange |
| 284 | H | " | " | K₄ | —CH₃ | yellowish-red |

285: phenyl-1,3,4-thiadiazolyl—N=N—C₆H₄—N(C₂H₅)(C₂H₄—N⊕(C₂H₅)₂—C₂H₄—O—C₆H₄)  (SO₄⁻²)½  scarlet 286: (3-chloro-4-cyano-isothiazol-5-yl)—N=N—[2-methyl-C₆H₃]—N(C₂H₅)(C₂H₄—N⊕(C₂H₅)₂—C₂H₄—O—C₆H₄)  (SO₄⁻²)½  violet Table V-continued

| Ex. | R₃ | R₅ | R'₁₂ | K⊕ | R₄ | I |
|---|---|---|---|---|---|---|
| 287 | (structure with dibromophenyl-thiazole) | | -N(CH₃)- phenyl- | -CH₂-CH(CH₃)-N⊕(C₂H₅)₂-C₂H₄O-phenyl | ⊖(SO₄⁻²)½ | red |
| 288 | (nitro-benzisothiazole) | | -N(C₂H₅)(CH₃-phenyl)-C₂H₄- | -N⊕(C₂H₅)₂-C₂H₄-O-phenyl | (SO₄⁻²)½ | blue |
| 289 | (nitro-thiazole) | | -N(C₂H₅)(CH₃-phenyl)-C₂H₄- | -N⊕(C₂H₅)₂-C₂H₄-O-phenyl | (SO₄⁻²)½ | violet |
| 290 | (dicyano-methylthiophene) | | -N(C₂H₅)(CH₃-phenyl)-C₂H₄- | -N⊕(C₂H₅)₂-C₂H₄-O-phenyl | (SO₄⁻²)½ | violet |
| 291 | (methyl-COOCH₃-CN-thiophene) | | -N(C₂H₅)(phenyl)-C₂H₄- | -N⊕(C₂H₅)₂-C₂H₄-O-phenyl | (SO₄⁻²)½ | reddish-violet |
| 292 | (chlorophenyl with ⊕N(CH₃)₂-C₂H₄-O-phenyl) | | -N(C₂H₄CN)(C₂H₅)- CH₃-phenyl | | Cl⊖ | orange |
| 293 | (chlorophenyl with ⊕N(CH₃)₂-C₂H₄-O-phenyl) | | -NH-C₂H₄-CN, Cl-phenyl | | ZnCl₃⊖ | golden-yellow |
| 294 | (dichloro-(CH₃)₂N-SO₂-phenyl) | | -N(C₂H₅)-phenyl-C₂H₄-O-phenyl-⊕N(CH₃)₂-C₂H₄-O-phenyl | | Cl⊖ | scarlet |

| Ex. | R'3 | R'5 | R12 | K⊕ | R'4 | I |
|-----|-----|-----|-----|-----|-----|---|
| 295 | | | | | 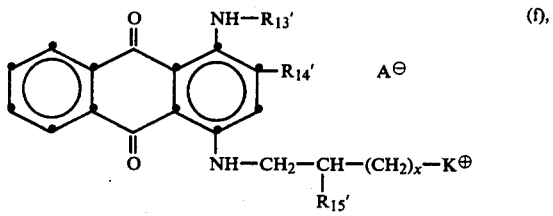 | red |

EXAMPLE 296

94.8 Parts 1-methylamino-4-bromoanthraquinone and 1 part copper acetate are added to 90 parts 1-dimethylamino-3-aminopropane and are stirred at 90° to 100° until the condensation reaction is finished as determined by thin-layer chromatography. The mixture is diluted with water until the reaction product begins to separate out. After cooling, the blue dye is filtered with suction, washed with neutral water and dried.

50.5 Parts of the fine pulverized dye so obtained is dissolved in 1000 parts dichlorobenzene and mixed with 31.2 parts 1-phenoxy-2-chloroethane, at 150° and is afterwards stirred at this temperature for 1 hour. After cooling the separated dye is filtered with suction, washed with toluene and dried under vacuum at 50° to 60°. 53 Parts of the blue dye of the formula

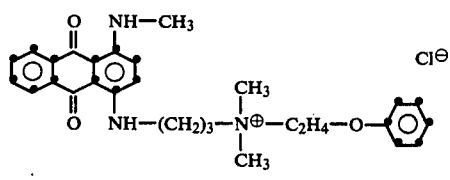

are obtained which dye gives fast blue dyeings on polyacrylonitrile and acid-modified polyamide fibres.

EXAMPLE 297

In place of 1-phenoxy-2-chloroethane as used in Example 296, 36 parts 1-phenoxy-4-chlorobutene-2 is used, employing the same procedure as described in Example 296, to obtain a similar dye of the formula

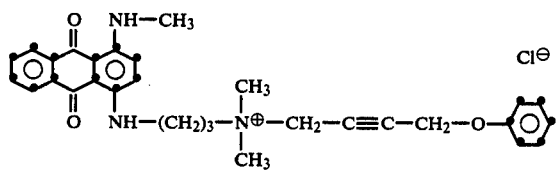

which on polyacrylonitrile and acid-modified polyamide fibres gives fast dyeings of a blue shade.

The structural composition of further dyes is shown in Table VI. The dyes may be obtained according to the procedure of the processes hereinbefore described and they correspond with the formula $$\text{(f)}$$

[anthraquinone structure with $NH-R_{13}'$, $R_{14}'$, $A^\ominus$, and $NH-CH_2-CH-(CH_2)_x-K^\oplus$ with $R_{15}'$]

in which $R_{13}'$ to $R_{15}'$, $K^\oplus$ and X have the significances as shown in the columns of the Table. A further column indicates the dye shade on polyacrylonitrile. The anion $A^\ominus$ may be any one of those named in the foregoing description.

Table VI

| Ex. | R14' | R15' | X | K⊕ | R13' | I |
|-----|------|------|---|-----|------|---|
| 298 | H | H | 1 | K2 | —CH3 | blue |
| 299 | H | H | 1 | K13 | " | " |
| 300 | H | H | 1 | K17 | " | " |
| 301 | H | H | 1 | K18 | " | " |
| 302 | H | H | 1 | K19 | " | " |
| 303 | H | H | 1 | K35 | " | " |
| 304 | H | H | 1 | K43 | " | " |
| 305 | H | H | 1 | K46 | " | " |
| 306 | H | H | 1 | K2 | —C6H5 | " |
| 307 | H | —OH | 1 | K2 | —CH3 | " |
| 308 | H | H | 2 | K2 | " | " |
| 309 | H | H | 1 | K1 | —C6H4—CH3 | greenish-blue |
| 310 | H | H | 1 | K2 | " | greenish-blue |
| 311 | H | H | 1 | K13 | " | greenish-blue |
| 312 | H | H | 1 | K17 | " | greenish-blue |
| 313 | H | H | 1 | K18 | " | greenish-blue |
| 314 | H | H | 1 | K19 | " | greenish-blue |
| 315 | H | H | 1 | K35 | " | greenish-blue |
| 316 | H | H | 1 | K44 | " | greenish-blue |
| 317 | H | H | 1 | K46 | —C6H4—CH3 | greenish-blue |
| 318 | H | —OH | 1 | K2 | " | greenish-blue |
| 319 | —CN | H | 1 | K2 | —CH3 | greenish-blue |
| 320 | —CONH2 | H | 1 | K2 | " | greenish-blue |
| 321 | —Br | H | 1 | K2 | " | greenish-blue |

Table VIII-continued

| Ex. | R$_{17}'$ | R$_{18}'$ | R$_{19}'$ | R$_{20}'$ | Y$_1$ | K$^\oplus$ | I |
|---|---|---|---|---|---|---|---|
| 360 | | | | | | 2Cl$^\ominus$ | blue |
| 361 | | | | | | 2Cl$^\ominus$ | red |
| 362 | | | | | | 2Cl$^\ominus$ | red |
| 363 | | | | | | 2Cl$^\ominus$ | blue |
| 364 | | | | | | 2Cl$^\ominus$ | yellow |

APPLICATION EXAMPLE A

20 Parts of the salt of the dye described in Example 1 and 80 parts dextrin are ground for 4 hours in a powder mill. 1 Part of the preparation so obtained is made into a paste with 1 part 40% acetic acid, then 200 parts demineralized water are poured onto the paste and the mixture is boiled for a short time. (The same dye and dextrin mixture can also be formed into a paste with 100 parts water and finally be spray dried.) The mixture is then diluted with 7000 parts demineralized water, mixed with 2 parts glacial acetic acid and is put into a bath at 60° with 100 parts polyacrylonitrile fabric. The fabric may be pretreated for 10 to 15 minutes at 60° in a bath consisting of 8000 parts water and 2 parts glacial acetic acid.

The dyebath is raised to 98° to 100° over a period of 30 minutes, boiled for 1½ hours and the fabric is rinsed. A bluish-red dyeing with good light and wet fastness properties is obtained.

10 Parts of the dye mentioned in Example 1 are dissolved in 60 parts glacial acetic acid and 30 parts water. A stable concentrated solution, with a dye content of about 10%, is obtained, which solution can be used to dye polyacrylonitrile according to the above-mentioned process.

APPLICATION EXAMPLE B

20 Parts of the dye from Example 1 are mixed with 80 parts dextrin in a ball-mill for 48 hours; 1 part of the preparation so obtained is made into a paste with 1 part 40% acetic acid, 200 parts demineralized water are poured onto the paste and the mixture is boiled for a short time. With this solution the following dyeings are made:

(a) The solution is diluted with 7000 parts of demineralized water and mixed with 21 parts of anhydrous sodium sulphate, 14 parts of ammonium sulphate, 14 parts of formic acid and 15 parts of a carrier, based on the reaction product of ethylene oxide with dichlorophenolene, are put into a bath at 60° with 100 parts of a polyester fabric, which fabric has been modified with acid groups. The fabric may be pretreated for 10 to 15 minutes at 60° in a bath consisting of 8000 parts of water and 2 parts of glacial acetic acid.

EXAMPLE 322

40.5 Parts of monochloromethylated 1-methylamino-4-(2',4'-xylidine)-anthraquinone, (obtained by reacting 1-methylamino-4-(2',4'-xylidene)-anthraquinone with dichlorodimethylether) are dissolved in 450 parts methanol at 50° and at this temperature is added dropwise to a solution of 15 parts diethylamine in 40 parts methanol. The solution is heated to its boiling point and then cooled to 40°, and a solution of 15.7 parts 2-phenoxy-1-chloroethane in 30 parts methanol is added thereto. The mixture is heated to its boiling point and then left to cool. The precipitated dye is filtered and washed with 50 parts methanol. After drying 41.4 parts of a dye of the formula

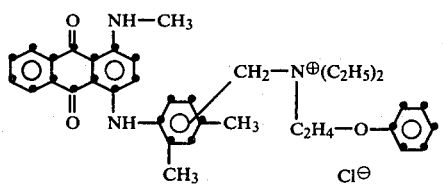

is obtained which on polyacrylonitrile and acidmodified polyester and polyamide fibres gives fast dyeings of a greenish-blue shade.

The structural composition of further dyes is given in Table VII. They can be prepared in accordance with the procedure of Example 322 and correspond to the formula

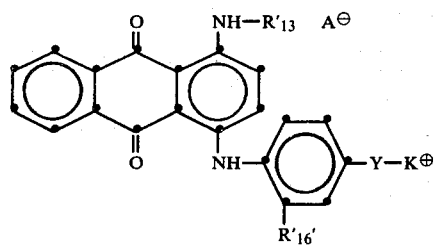

in which $R_{13}'$, $R_{16}'$, Y and $K^{\oplus}$ have the significances as shown in the columns. A further column I indicates the shade of dyeing obtained on polyacrylonitrile. The anion $A^{\ominus}$ may be any one of those named in the foregoing description.

Table VII

| Ex. | $R'_{13}$ | $R'_{16}$ | $K^{\oplus}$ | Y | I |
|---|---|---|---|---|---|
| 323 | H | H | $K_2$ | —$CH_2$— | reddish-blue |
| 324 | H | H | $K_{13}$ | " | " |
| 325 | H | H | $K_{17}$ | " | " |
| 326 | H | H | $K_{18}$ | " | " |
| 327 | H | H | $K_{19}$ | " | " |
| 328 | H | H | $K_{35}$ | " | " |
| 329 | H | H | $K_{43}$ | " | " |
| 330 | H | H | $K_{44}$ | " | " |
| 331 | H | H | $K_1$ | —O—$C_2H_4$— | " |
| 332 | H | H | $K_2$ | " | " |
| 333 | H | H | $K_{13}$ | " | " |
| 334 | H | H | $K_{17}$ | " | " |
| 335 | H | H | $K_{18}$ | " | " |
| 336 | H | H | $K_{19}$ | " | " |
| 337 | H | H | $K_{35}$ | " | " |
| 338 | H | H | $K_{43}$ | " | " |
| 339 | H | H | $K_{44}$ | " | " |
| 340 | H | H | $K_{45}$ | —$CH_2$— | " |
| 341 | H | H | $K_{46}$ | " | " |
| 342 | H | H | $K_{45}$ | —O—$C_2H_4$— | " |
| 343 | H | H | $K_{46}$ | " | " |
| 344 | —$CH_3$ | —$CH_3$ | $K_1$ | —$CH_2$— | greenish-blue |
| 345 | " | " | $K_2$ | " | " |
| 346 | " | " | $K_{13}$ | " | " |
| 347 | " | " | $K_{17}$ | " | " |
| 348 | " | " | $K_{18}$ | " | " |
| 349 | " | " | $K_{19}$ | " | " |
| 350 | " | " | $K_{35}$ | " | " |
| 351 | " | " | $K_{43}$ | " | " |
| 352 | " | " | $K_{44}$ | " | " |
| 353 | " | " | $K_{45}$ | " | " |
| 354 | " | " | $K_{46}$ | " | " |
| 355 | " | " | $K_4$ | " | " |

The structural composition of further dyes is shown in Table VII. They may be prepared in accordance with the procedure of the foregoing Examples and correspond with the formula

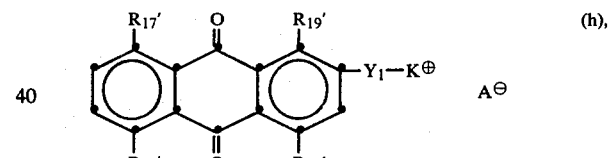

in which $Y_1$, $R_{17}'$ to $R_{20}'$ and $K^{\oplus}$ have the significances as shown in the columns. A further column I indicates the shade on dyeing on polyacrylonitrile. The anion $A^{\ominus}$ may be any one of those named in the foregoing description.

Table VIII

| Ex. | $R_{17}'$ | $R_{18}'$ | $R_{19}'$ | $R_{20}'$ | $Y_1$ | $K^{\oplus}$ | I |
|---|---|---|---|---|---|---|---|
| 356 | H | H | —$NH_2$ | —NH—$CH_3$ | —CO—NH—$C_2H_4$— | $K_2$ | greenish-blue |
| 357 | H | H | —$NH_2$ | —NH—C₆H₅ | —O—$C_2H_4$— | $K_2$ | bluish-violet |
| 358 | —OH | —$NH_2$ | —$NH_2$ | —OH | —C₆H₄—O—$C_2H_4$— | $K_2$ | blue |
| 359 | H | H | —$NH_2$ | —NH—$CH_3$ | —CO—NH—$C_3H_7$— | $K_6$ | greenish-blue |

The dyebath is raised to 98°-100° over a period of 30 minutes, boiled for 1½ hours and the fabric rinsed. A similar bluish-red dyeing with good wet fastness is obtained.

(b) The solution is diluted with 3000 parts of demineralized water and mixed with 18 parts of anhydrous sodium sulphate, together with 6 parts of ammonium sulphate and formic acid and put into the bath at 60° with 100 parts of a polyester fabric, which fabric has been modified with acid groups. The closed vessel is heated to 110° over a period of 45 minutes, kept at this temperature for one hour with shaking, cooled to 60° within 25 minutes and the dyed fabric rinsed. A similar bluish-red dyeing with good wet fastness is obtained.

(c) The same procedure as described in paragraph (b) above is carried out except that the closed vessel is heated for one hour at 120°.

Formulae of representative dyes of the foregoing Examples are as follows:

EXAMPLE 1

EXAMPLE 55

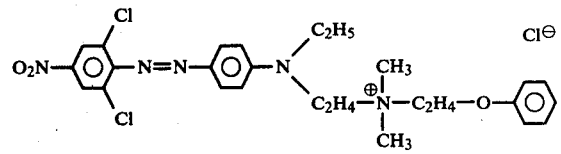

EXAMPLE 72

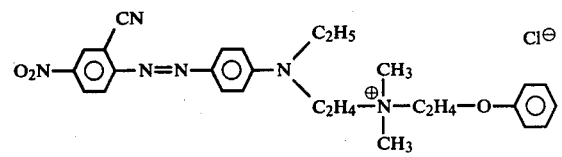

EXAMPLE 75

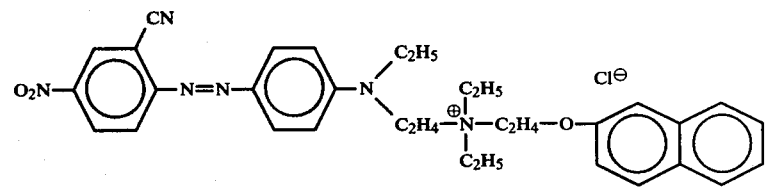

EXAMPLE 82

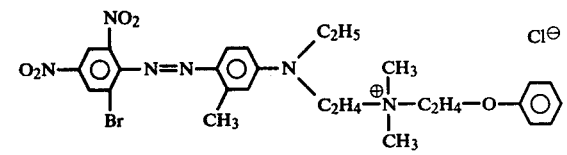

EXAMPLE 103

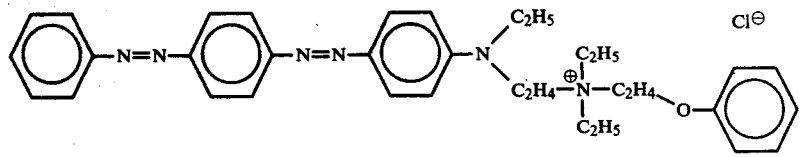

EXAMPLE 115

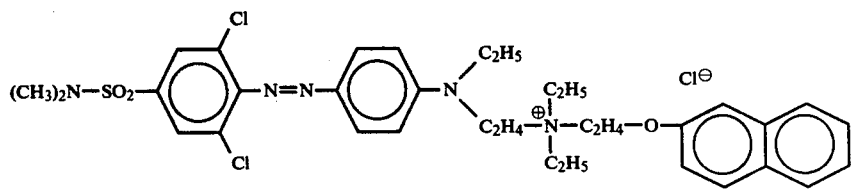

EXAMPLE 124
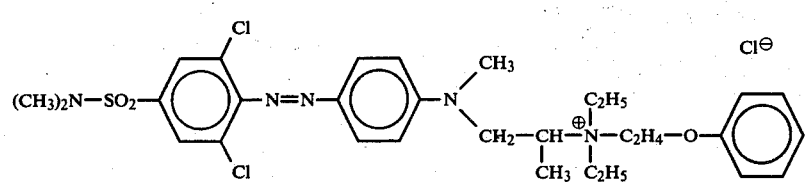
EXAMPLE 149
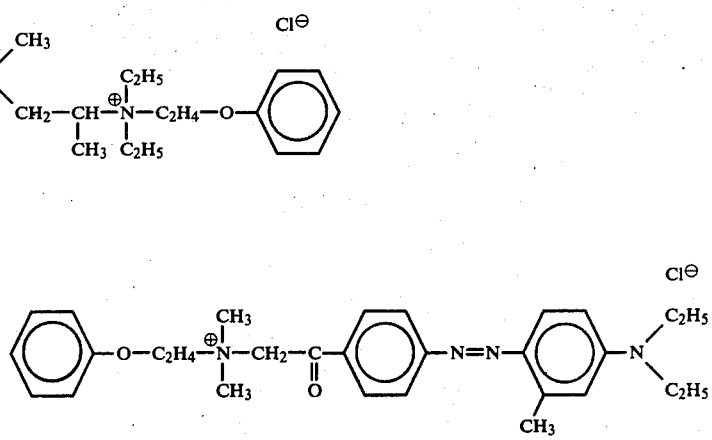
EXAMPLE 128
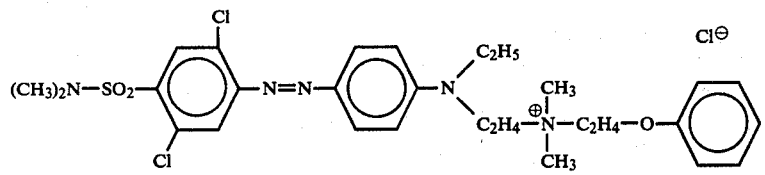
EXAMPLE 162
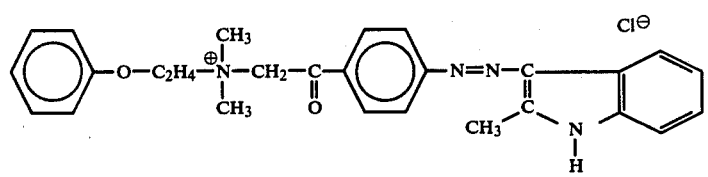
EXAMPLE 135
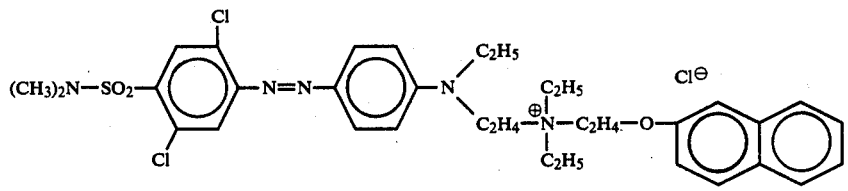
EXAMPLE 190
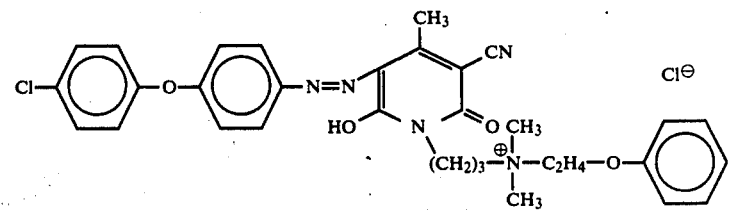

EXAMPLE 210
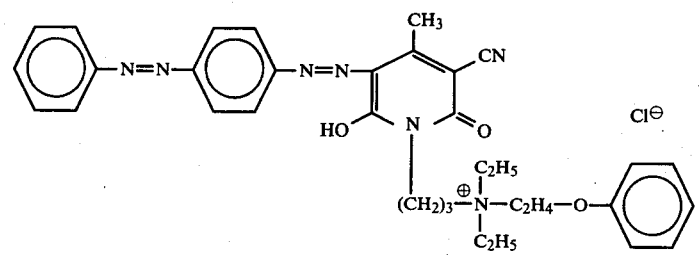
EXAMPLE 242
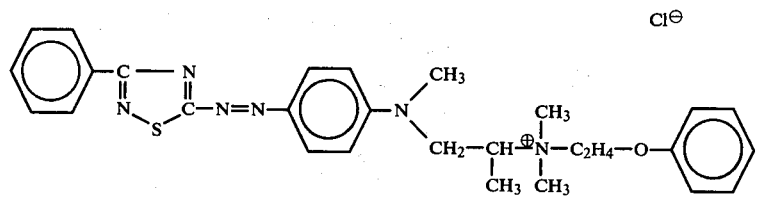
EXAMPLE 257
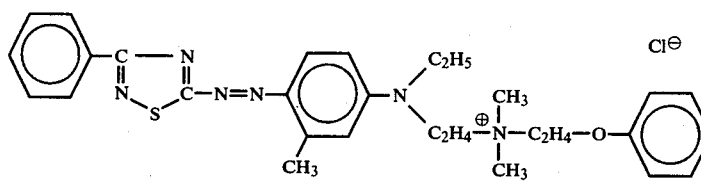
EXAMPLE 285
EXAMPLE 292
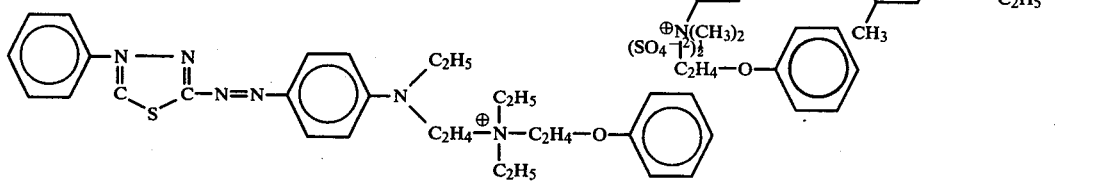
EXAMPLE 294
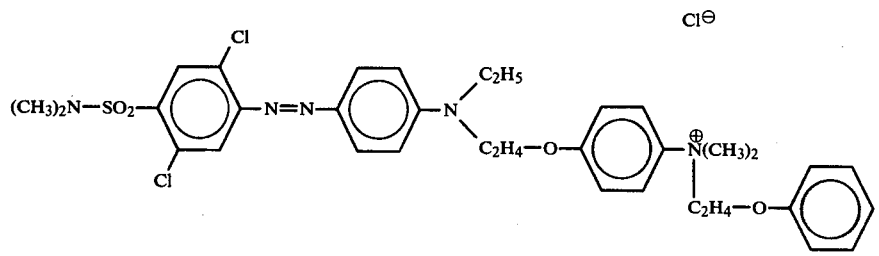

EXAMPLE 295

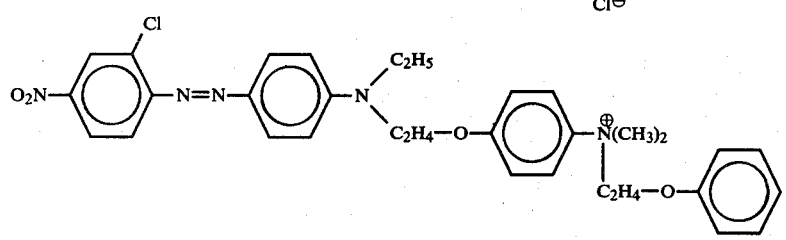

EXAMPLE 296

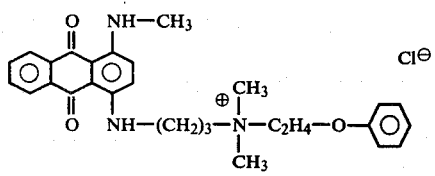

EXAMPLE 309

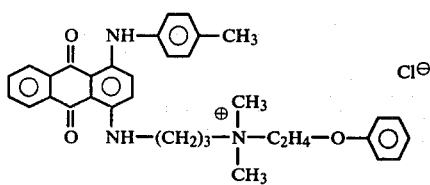

EXAMPLE 322

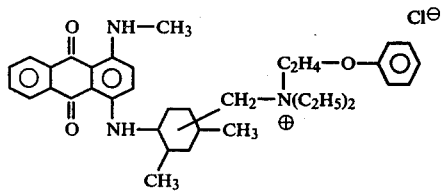

EXAMPLE 323

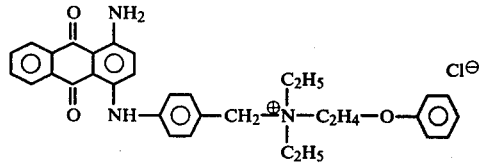

EXAMPLE 331

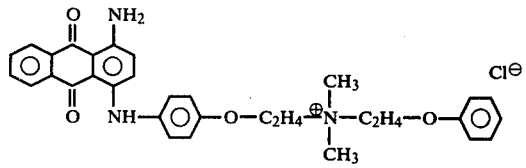

EXAMPLE 356

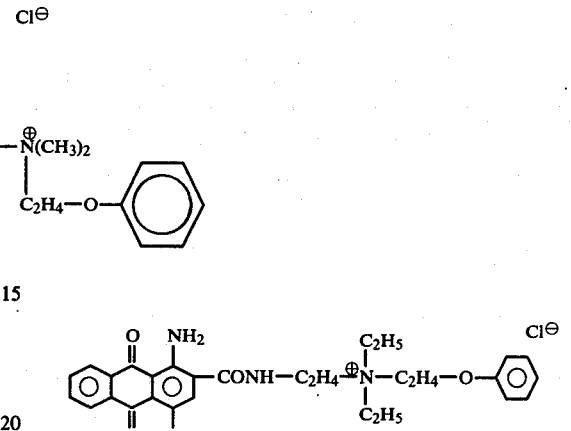

EXAMPLE 358

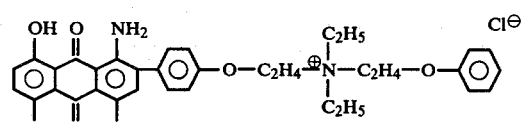

What is claimed is:
1. A basic dye of the formula

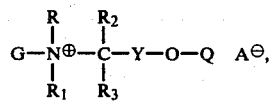

wherein G is the residue of a dye other than a carbocyclic monoazo dye,
R is $C_{1-4}$alkyl; $C_{1-4}$alkyl substituted by hydroxy or phenyl; amino or $C_{1-4}$alkoxy,
$R_1$ is $C_{1-4}$alkyl or $C_{1-4}$alkyl substituted by hydroxy or phenyl, or

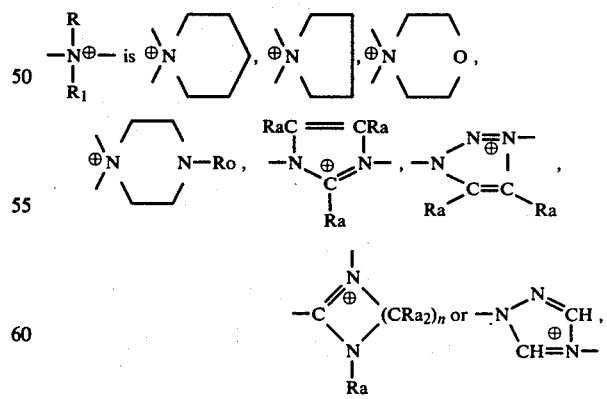

wherein each Ra is independently hydrogen or $C_{1-4}$alkyl,
Ro is $C_{1-4}$alkyl or phenyl, and
n is 1 or 2,
$R_2$ is hydrogen or $C_{1-4}$alkyl, $R_3$ is hydrogen or $C_{1-4}$alkyl,

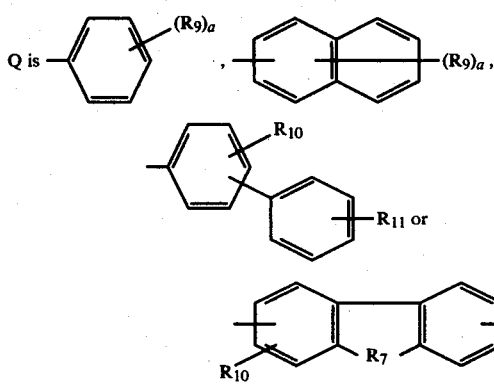

wherein $R_7$ is —S—, —O—, —CO—, —SO—,

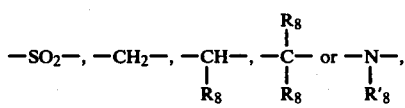

wherein each $R_8$ is independently $C_{1-4}$alkyl, and $R_8'$ is hydrogen or $C_{1-4}$alkyl, each $R_9$ is independently hydroxy; halo; $C_{1-4}$alkyl; $C_{1-4}$alkyl substituted by halo, hydroxy, cyano, phenyl or phenoxy; $C_{1-4}$alkoxy; $C_{1-4}$-alkoxy substituted by halo, hydroxy, cyano, phenyl or phenoxy; $C_{5-6}$cycloalkyl; $C_{5-6}$-cycloalkyl substituted by $C_{1-4}$-alkyl; trifluoromethyl; cyano; nitro; phenoxy; naphthyloxy; phenylazo; —CO—Ro; —CO—O—Ro; —O—CO—Ro; —CO—NH—Ro; —CO—N(Ro)$_2$; —O—CO—N(Ro)$_2$; —N-H—CO—Ro; —SO$_2$—Ro; —SO$_2$—NH—Ro; —O—SO$_2$—N(Ro)$_2$;

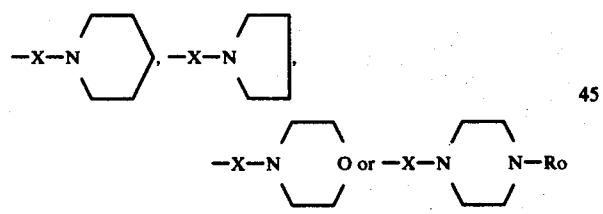

wherein each Ro is independently $C_{1-4}$alkyl or phenyl, and
X is —CO— or —SO$_2$—,
$R_{10}$ is hydrogen, halo or $C_{1-4}$-alkyl,
$R_{11}$ is hydrogen, $C_{1-4}$alkyl, $C_{1-4}$-alkoxy, phenyl, phenoxy, halo, trifluoromethyl, nitro, cyano, —CO—Ro, —CO—O—Ro, —O—CO—Ro, —CO—NH—Ro, —NH—CO—Ro, —SO$_2$—Ro, —SO$_2$—NH—Ro or —SO$_2$N(Ro)$_2$,
wherein each Ro is independently $C_{1-4}$alkyl or phenyl, and
a is 0, 1, 2, 3, 4 or 5, with the proviso that each $R_9$ must be halo when a is 4 or 5, Y is 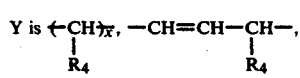

-continued

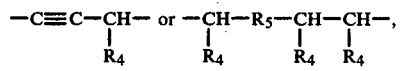

wherein each $R_4$ is independently hydrogen or $C_{1-4}$alkyl,
$R_5$ is —O—, —S—,

—SO—, —SO$_2$— or —CO—,
wherein $R_6$ is hydrogen or $C_{1-4}$alkyl, and
x is 1 to 6, and
$A^\ominus$ is an anion,
wherein each halo is independently chloro, bromo or iodo, with the proviso that the molecule is free of sulfo groups.

2. A dye according to claim 1 wherein G is the residue of a heterocyclic azo dye or a carbocyclic disazo dye.

3. A dye according to claim 2 wherein G is the residue of a heterocyclic azo dye.

4. A dye according to claim 3 wherein G is the residue of a heterocyclic azo dye containing a thiadiazole, thiazole, benzothiazole, isothiazole or benzoisothiazole ring.

5. A dye according to claim 2 wherein R is $C_{1-4}$alkyl; $C_{1-4}$alkyl substituted by hydroxy or phenyl; amino or $C_{1-4}$alkoxy,
$R_1$ is $C_{1-4}$alkyl or $C_{1-4}$alkyl substituted by hydroxy or phenyl,
$R_7$ is —CO—, —CH$_2$—,

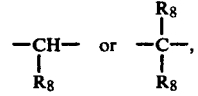

wherein each $R_8$ is independently $C_{1-4}$alkyl, and
each $R_9$ is independently hydroxy; halo; $C_{1-4}$alkyl; $C_{1-4}$-alkyl substituted by halo, hydroxy, cyano, phenyl or phenoxy; $C_{1-4}$alkoxy; $C_{1-4}$alkoxy substituted by halo, hydroxy, cyano, phenyl or phenoxy; $C_{5-6}$cycloalkyl; $C_{5-6}$cycloalkyl substituted by $C_{1-4}$alkyl; trifluoromethyl; cyano; nitro; phenoxy; naphthyloxy; phenylazo; —CO—Ro; —CO—O—Ro; —O—CO—Ro; —CO—NH—Ro; —CO—N(Ro)$_2$; —O—CO—N(Ro)$_2$; —N-H—CO—Ro; —SO$_2$—Ro; —SO$_2$—NH—Ro or —O—SO$_2$—N(Ro)$_2$,
wherein each Ro is independently $C_{1-4}$alkyl or phenyl.

6. A dye according to claim 5 wherein G is the residue of a heterocyclic azo dye.

7. A dye according to claim 6 wherein G is the residue of a heterocyclic azo dye containing a thiadiazole, thiazole, benzothiazole, isothiazole or benzoisothiazole ring.

8. A dye according to claim 7 wherein R is $C_{1-4}$alkyl, and
$R_1$ is $C_{1-4}$alkyl.

9. A dye according to claim 8 wherein $R_2$ is hydrogen or methyl, and
$R_3$ is hydrogen or methyl.

10. A dye according to claim 9 wherein Y is $$-(CH)_{x'}-,$$
$$\quad\quad |$$
$$\quad\quad R_4$$

—CH=CH—CH₂—, —C≡C—CH₂— or —CH₂—O—CH₂CH₂—, wherein each $R_4$ is independently hydrogen or $C_{1-4}$alkyl, and x' is 1, 2 or 3.

11. A dye according to claim 10 wherein Q is phenyl; naphthyl; biphenylyl; phenyl substituted by halo, $C_{1-4}$alkyl, $C_{1-4}$alkoxy, trifluoromethyl, cyano or nitro or phenyl substituted by 2 to 5 chloro substituents.

12. A dye according to claim 7 having the formula $$[D-N=N-K-]-W_{q'}-T]_t,$$

wherein D is a diazo component radical containing a thiadiazole, thiazole, benzothiazole, isothiazole or benzoisothiazole ring, K is a coupling component radical, each T is independently $$\overset{R}{\underset{R_1}{\overset{|}{\oplus}N}}-\overset{R_2}{\underset{R_3}{\overset{|}{C}}}-Y-O-Q \quad A^{\ominus},$$

each W is independently divalent bridging radical, each q' is independently 0 or 1, and t is 1 or 2, with the proviso that each —$W_{q'}$—T independently is bound to D or K.

13. A compound of the formula $$D'-N=N-K'-N\overset{R_{16}}{\underset{R_{17}}{\big\backslash}}\overset{R}{\underset{R_1}{\overset{|}{N}\oplus}}-\overset{R^2}{\underset{R_3}{\overset{|}{C}}}-Y-O-Q \quad A^{\ominus},$$

wherein D' is $R_{23}$—C═N, N—N
         N—S—C—, $R_{23}'$—C—S—C—,

[isothiazole with $R_{23}''$, $R_{23}'''$], [benzene with $R_g$, $R_{g'}$ and S—C═N],

[benzothiazole], or [thiazole with $R_i$, $R_h$]

$$[CH_3O\text{-benzene with }S, N\text{-}CH_3\text{, }C\text{=, }A^{\ominus}]$$

wherein $R_{23}$ is hydrogen; phenyl; phenyl substituted by $C_{1-4}$alkyl, cyano or nitro; $C_{1-4}$alkylsulfonyl; $C_{1-4}$alkylsulfinyl; $C_{1-4}$alkylthio; halo or $C_{1-4}$alkyl, $R_{23}'$ is hydrogen, $C_{1-4}$alkyl, phenyl or phenyl substituted by $C_{1-4}$alkyl, cyano, nitro or halo, $R_{23}''$ is halo, $R_{23}'''$ is cyano, —CO—NH—Ra or —CO—O—Ro, wherein Ra is hydrogen or $C_{1-4}$alkyl, and Ro is $C_{1-4}$alkyl or phenyl, $R_g$ is halo, nitro or —CO—Ro, wherein Ro is $C_{1-4}$alkyl or phenyl, $R_{g'}$ is halo, $R_h$ is nitro, cyano or trifluoromethyl, $R_i$ is nitro or cyano, and $A^{\ominus}$ is an anion, K' is [phenyl with $R_{18}$] or [naphthyl], wherein $R_{18}$ is hydrogen, $C_{1-4}$alkyl, $C_{1-4}$alkoxy or halo, R is $C_{1-4}$alkyl; $C_{1-4}$alkyl substituted by hydroxy or phenyl; $C_{1-4}$alkoxy or amino, $R_1$ is $C_{1-4}$alkyl of $C_{1-4}$alkyl substituted by hydroxy or phenyl, $$-\overset{R}{\underset{R_1}{\overset{|}{N\oplus}}}- \text{ is } \oplus N\text{[piperidine]}, \oplus N\text{[pyrrolidine]}, \oplus N\text{[morpholine]}O,$$

$$\oplus N\text{[piperazine]}N\text{-Ro}, -N\overset{RaC=CRa}{\underset{Ra}{\overset{\oplus}{C}}}N\text{-}, -N\overset{N=N}{\underset{Ra}{\overset{|}{C=C}}}\overset{|}{Ra},$$

$$-C\overset{N}{\underset{N}{\overset{\oplus}{=}}}(CRa_2)_n \text{ or } -N\overset{N=CH}{\underset{CH=N}{\oplus|}}-$$
$$\quad\quad\quad\quad Ra$$

wherein each Ra is independently hydrogen or $C_{1-4}$alkyl,

Ro is $C_{1-4}$alkyl or phenyl, and n is 1 or 2, $R_2$ is hydrogen or $C_{1-4}$alkyl, $R_3$ is hydrogen or $C_{1-4}$alkyl, $R_{16}$ is hydrogen, $C_{1-4}$alkyl, phenyl or $C_{1-4}$alkyl substituted by halo, hydroxy, cyano, phenyl, phenoxy, ($C_{1-4}$alkoxy)carbonyl, ($C_{1-4}$alkyl)carbonyloxy, $C_{1-4}$alkoxy, benzoyloxy, —O—CO—N(Ra)₂ or —CO—N(Ra)₂, wherein each Ra is independently hydrogen or C$_{1-4}$alkyl,

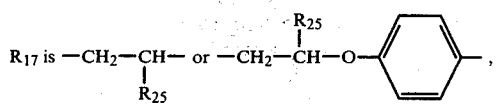

wherein R$_{25}$ is hydrogen or C$_{1-4}$alkyl,

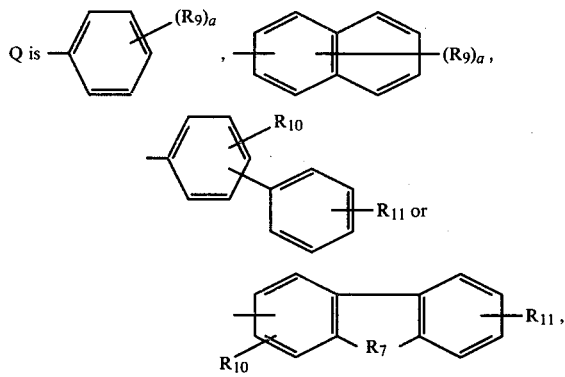

wherein R$_7$ is —S—, —O—, —CO—, —SO—, —SO$_2$—, —CH$_2$—, $$-\overset{R_8}{\underset{R_8}{C}}-, \quad -\overset{R_8}{\underset{R_8}{C}}- \quad \text{or} \quad -\underset{R_{8'}}{N}-,$$

wherein each R$_8$ is independently C$_{1-4}$alkyl, and R$_{8'}$ is hydrogen or C$_{1-4}$alkyl, each R$_9$ is independently hydroxy; halo; C$_{1-4}$alkyl; C$_{1-4}$alkyl substituted by halo, hydroxy, cyano, phenyl or phenoxy; C$_{1-4}$alkoxy; C$_{1-4}$-alkoxy substituted by halo, hydroxy, cyano, phenyl or phenoxy; C$_{5-6}$cycloalkyl; C$_{5-6}$-cycloalkyl substituted by C$_{1-4}$-alkyl; trifluoromethyl; cyano; nitro; phenoxy; naphthyloxy; phenylazo; —CO—Ro; —CO—O—Ro; —O—CO—Ro; —CO—NH—Ro; —CO—N(Ro)$_2$; —O—CO—N(Ro)$_2$; —NH—CO—Ro; —SO$_2$—Ro; —SO$_2$—NH—Ro; —O—SO$_2$—N(Ro)$_2$;

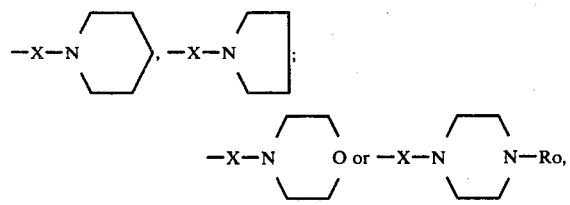

wherein each Ro is independently C$_{1-4}$alkyl or phenyl, and
X is —CO— or —SO$_2$—;
R$_{10}$ is hydrogen, halo or C$_{1-4}$alkyl,
R$_{11}$ is hydrogen, C$_{1-4}$alkyl, C$_{1-4}$alkoxy, phenyl, phenoxy, halo, trifluoromethyl, nitro, cyano, —CO—Ro, —CO—O—Ro, —O—CO—Ro, —CO—NH—Ro, —NH—CO—Ro, —SO$_2$—Ro, —SO$_2$—NH—Ro or —SO$_2$N(Ro)$_2$, wherein each Ro is independently C$_{1-4}$alkyl or phenyl, and
a is 0, 1, 2, 3, 4 or 5, with the proviso that each R$_9$ must be halo when a is 4 or 5,

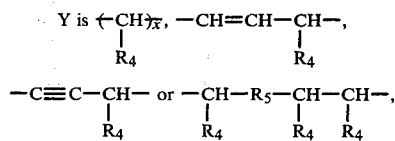

wherein each R$_4$ is independently hydrogen or C$_{1-4}$alkyl,
R$_5$ is —O—, —S—, $$-\underset{R_6}{N}-,$$

—SO—, —SO$_2$— or —CO—,
wherein R$_6$ is hydrogen or C$_{1-4}$alkyl, and
x is 1 to 6, and
A$^\ominus$ is an anion,
wherein each halo is independently chloro, bromo or iodo.

14. A compound according to claim 13
wherein R is C$_{1-4}$alkyl; C$_{1-4}$alkyl substituted by hydroxy or phenyl; amino or C$_{1-4}$alkoxy, and
R$_1$ is C$_{1-4}$alkyl or C$_{1-4}$alkyl substituted by hydroxy or phenyl.

15. A compound according to claim 14
wherein R is C$_{1-4}$alkyl, and
R$_1$ is C$_{1-4}$alkyl.

16. A compound according to claim 15
wherein R$_2$ is hydrogen or methyl, and
R$_3$ is hydrogen or methyl.

17. A compound according to claim 16
wherein Y is $$-(\text{CH})_{\overline{x}}-,$$
$$\underset{R_4}{|}$$

—CH=CH—CH$_2$—, —C≡C—CH$_2$— or —CH$_2$—O—CH$_2$—CH$_2$—,
wherein each R$_4$ is independently hydrogen or C$_{1-4}$alkyl, and
x' is 1, 2 or 3.

18. A compound according to claim 17
wherein Q is phenyl; naphthyl; biphenylyl; dibenzofuranyl; phenyl substituted by halo, C$_{1-4}$alkyl, C$_{1-4}$alkoxy, trifluoromethyl, cyano or nitro or phenyl substituted by 2 to 5 chlorosubstituents.

19. A compound according to claim 18
wherein R is methyl or ethyl,
R$_1$ is methyl or ethyl,
R$_2$ is hydrogen, and
R$_3$ is hydrogen.

20. A compound according to claim 19
wherein Q is phenyl, phenyl substituted by 1 to 5 chloro substituents or 2-naphthyl, and
Y is —CH$_2$—.

21. A compound according to claim 13
wherein D' is

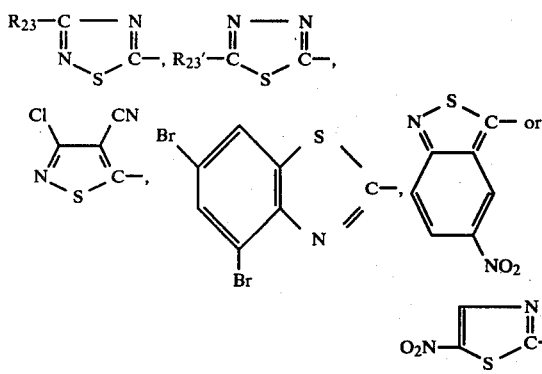

wherein $R_{23}$ is phenyl or 2-cyanophenyl, and $R_{23}'$ is phenyl.

22. A compound according to claim 21 wherein R is $C_{1-4}$alkyl, and
$R_1$ is $C_{1-4}$alkyl.

23. A compound according to claim 22

wherein $R_2$ is hydrogen or methyl, and
$R_3$ is hydrogen or methyl.

24. A compound according to claim 23 wherein Y is $+CH\rightarrow_{x'}$,
$\quad\quad\ \ |$
$\quad\quad\ \ R_4$ $-CH=CH-CH_2-$, $\quad -C\equiv C-CH_2-$ or $-CH-$
$2-O-CH_2-CH_2-$,
wherein each $R_4$ is independently hydrogen or $C_{1-4}$alkyl, and
x' is 1, 2 or 3.

25. A compound according to claim 24 wherein Q is phenyl; naphthyl; biphenylyl; dibenzofuranyl; phenyl substituted by halo, $C_{1-4}$alkyl, $C_{1-4}$alkoxy, trifluoromethyl, cyano or nitro or phenyl substituted by 2 to 5 chloro substituents.

26. A compound according to claim 25 wherein R is methyl or ethyl,
$R_1$ is methyl or ethyl,
$R_2$ is hydrogen, and
$R_3$ is hydrogen.

27. A compound according to claim 26 wherein Y is $-CH-$,
$\ \ |$
$\ \ R_4''$ wherein $R_4''$ is hydrogen or methyl.

28. A compound according to claim 22 wherein Q is phenyl, phenyl substituted by 1 to 5 chloro substituents or 2-naphthyl, and
Y is $-CH_2-$.

29. A compound according to claim 28 having the formula

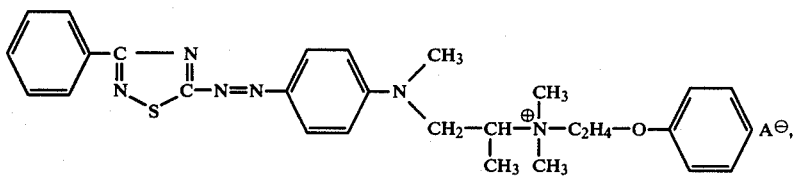

wherein $A^\ominus$ is an anion.

30. The compound according to claim 29 wherein $A^\ominus$ is chloride.

31. A compound according to claim 28 having the formula

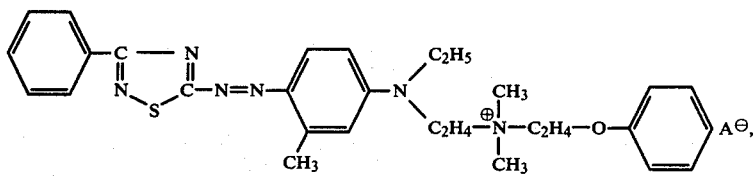

wherein $A^\ominus$ is an anion.

32. The compound according to claim 31 wherein $A^\ominus$ is chloride.

33. A compound according to claim 28 having the formula

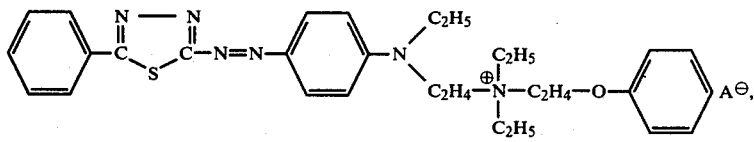

wherein $A^\ominus$ is an anion.

34. The compound according to claim 33 wherein $A^\ominus$ is sulfate.

35. A compound according to claim 28 having the formula

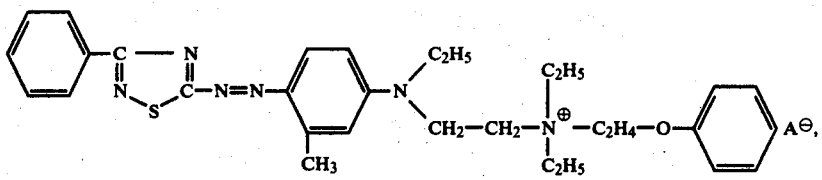

wherein $A^\ominus$ is an anion.

36. The compound according to claim 35 wherein $A^\ominus$ is chloride.

37. A dye according to claim 3 having the formula

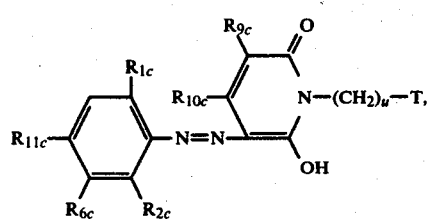

wherein each of $R_{1c}$ and $R_{2c}$ is independently hydrogen, $C_{1-4}$alkyl, halo, nitro, cyano or $C_{1-4}$alkoxy,
$R_{6c}$ is hydrogen, halo, $C_{1-4}$alkyl or $C_{1-4}$alkoxy,
$R_{11c}$ is hydrogen, phenoxy, halophenoxy, $C_{1-4}$alkoxy, $C_{1-4}$alkyl, ($C_{1-4}$alkoxy)carbonyl, phenylazo or ($C_{1-4}$alkyl)phenylazo, with the provisos that (i) at least one of $R_{1c}$, $R_{2c}$, $R_{6c}$ and $R_{11c}$ is hydrogen and (ii) when $R_{11c}$ is phenylazo or ($C_{1-4}$alkyl)phenylazo, $R_{2c}$ is hydrogen and each of $R_{1c}$ and $R_{6c}$ is independently hydrogen, $C_{1-4}$alkyl or $C_{1-4}$alkoxy,
$R_{9c}$ is hydrogen, cyano, halo or nitro,
$R_{10c}$ is $C_{1-4}$alkyl or phenyl,
u is 2 or 3, and T is 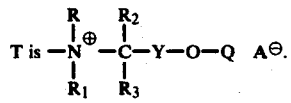

38. A dye according to claim 1
wherein R is $C_{1-4}$alkyl, and
$R_1$ is $C_{1-4}$alkyl.
39. A dye according to claim 38
wherein $R_2$ is hydrogen or methyl, and
$R_3$ is hydrogen or methyl.
40. A dye according to claim 39
wherein Y is

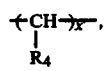

$-CH=CH-CH_2-$, $-C\equiv C-CH_2-$ or $-CH_2-O-CH_2-CH_2-$,
wherein each $R_4$ is independently hydrogen or $C_{1-4}$alkyl, and
$x'$ is 1, 2 or 3.
41. A dye according to claim 40
wherein Q is phenyl; naphthyl; biphenylyl; dibenzofuranyl; phenyl substituted by halo, $C_{1-4}$alkyl, $C_{1-4}$alkoxy, trifluoromethyl, cyano or nitro or phenyl substituted by 2 to 5 chloro substituents.
42. A dye according to claim 2 having the formula

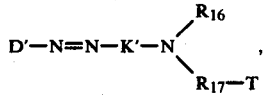

wherein D' is 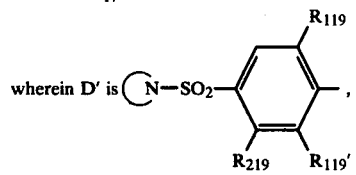

wherein each $R_{20}$ is independently hydrogen, $C_{1-4}$alkyl or $C_{1-4}$alkoxy,
each of $R_{119}$ and $R_{119}'$ is independently hydrogen, nitro, halo, cyano, $C_{1-4}$alkyl, trifluoromethyl, $C_{1-4}$alkylsulfonyl or $C_{1-4}$alkoxy,
$R_{219}$ is hydrogen, halo, nitro or cyano,
with the proviso that at least one of $R_{119}$, $R_{119}'$ and $R_{219}$ is hydrogen or halo,
$R_{319}$ is hydrogen, halo, nitro, cyano, trifluoromethyl or $C_{1-4}$alkylsulfonyl,
$R_{419}$ is hydrogen, halo, nitro, cyano, $C_{1-4}$alkyl or $C_{1-4}$alkoxy,
each of Rj and Rj" is independently cyano, ($C_{1-4}$alkoxy)carbonyl or $-CONHRa$,
wherein Ra is hydrogen or $C_{1-4}$alkyl,
Rj' is $C_{1-4}$alkyl or phenyl,

⟨N− is piperidino, morpholino, pyrrolidino or N'-($C_{1-4}$alkyl)piperazino, and
$A^\ominus$ is an anion K' is 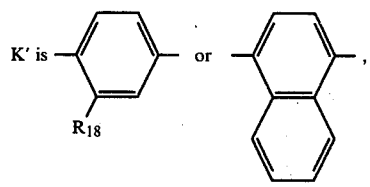 or , wherein $R_{18}$ is hydrogen, $C_{1-4}$alkyl, $C_{1-4}$alkoxy or halo, $R_{16}$ is hydrogen, $C_{1-4}$alkyl, phenyl or $C_{1-4}$alkyl substituted by halo, hydroxy, cyano, phenyl, phenoxy, ($C_{1-4}$alkoxy)carbonyl, ($C_{1-4}$alkyl)carbonyloxy, $C_{1-4}$alkoxy, benzoyloxy, —O—CO—N(Ra)$_2$ or —CO—N(Ra)$_2$, wherein each Ra is independently hydrogen or $C_{1-4}$alkyl, $R_{17}$ is 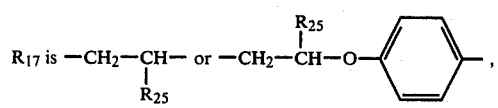, wherein $R_{25}$ is hydrogen or $C_{1-4}$alkyl, and T is 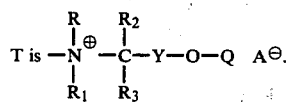.

43. A dye according to claim 3 having the formula

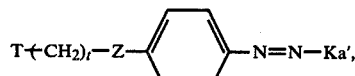

wherein Ka' is 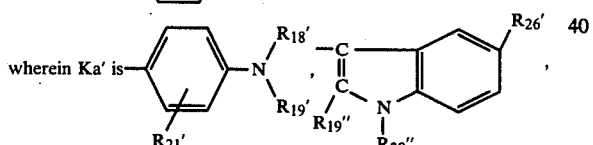

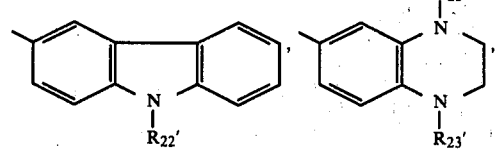

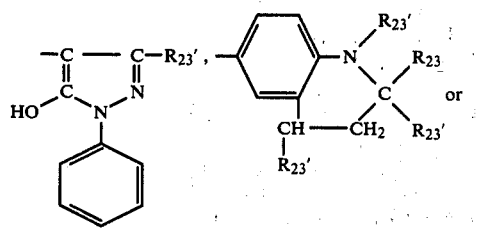

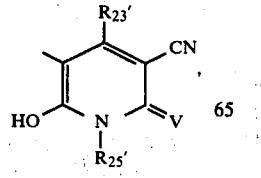

wherein $R_{18}'$ and $R_{19}'$ taken together and with the nitrogen atom to which they are joined are

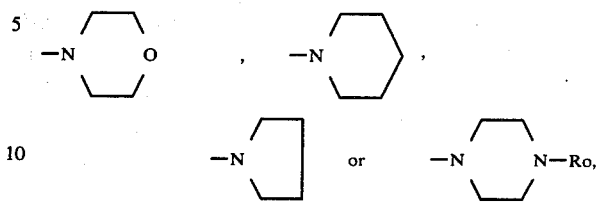

wherein Ro is $C_{1-4}$alkyl or phenyl,
$R_{19}''$ is phenyl, $C_{1-4}$alkyl or phenyl($C_{1-4}$alkyl),
$R_{20}''$ is hydrogen, phenyl or $C_{1-4}$alkyl,
$R_{21}'$ is hydrogen, $C_{1-4}$alkyl, $C_{1-4}$alkoxy or halo,
$R_{22}'$ is $C_{1-4}$alkyl,
each $R_{23}'$ is independently $C_{1-4}$alkyl,
$R_{25}'$ is hydrogen or $C_{1-4}$alkyl,
$R_{26}'$ is hydrogen, halo, $C_{1-4}$alkyl or $C_{1-4}$alkoxy, and
V is =O or =NH, T is 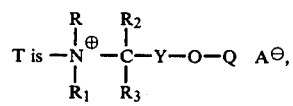, Z is —CO— or —SO$_2$—, and
t is 1 or 2.

44. A dye according to claim 1 having the formula

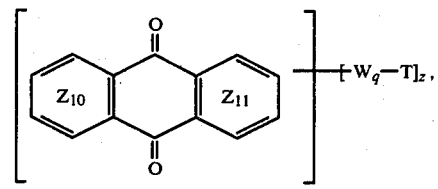

wherein each T is independently

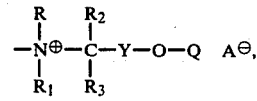

each W is independently a divalent bridging radical,
q' is independently 0 or 1,
z is 1 or 2,
with the provisos that (i) each —W$_{q'}$—T independently is bound to Ring Z$_{10}$ to Ring Z$_{11}$ and (ii) each of Ring Z$_{10}$ and Ring Z$_{11}$ is further unsubstituted or further substituted.

45. A dye according to claim 44 having the formula

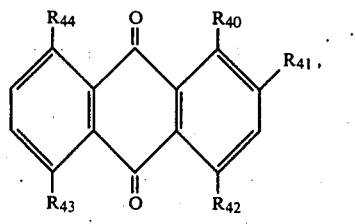

wherein $R_{40}$ is hydroxy, —NHR$_{46}$ or

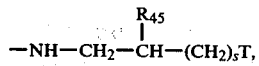

wherein $R_{45}$ is hydrogen or hydroxy,
$R_{46}$ is hydrogen, $C_{1-4}$alkyl, cyclohexyl, phenyl or phenyl substituted by one or two substituents selected from the group consisting of $C_{1-4}$alkyl, $C_{1-4}$alkoxy, benzyloxy and halo,

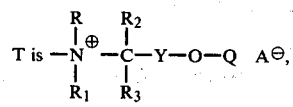

and s is 1 or 2,
$R_{41}$ is hydrogen, halo, cyano, —CONH$_2$,

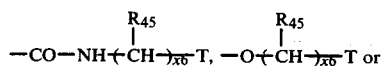

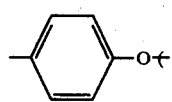

wherein each $R_{45}$ is independently hydrogen or hydroxy,

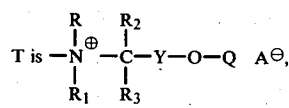

and x6 is 2, 3 or 4,
$R_{42}$ is —NH—$R_{46}$,

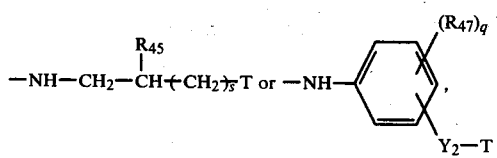

wherein $R_{45}$ is hydrogen or hydroxy,
$R_{46}$ is hydrogen, $C_{1-4}$alkyl, cyclohexyl, phenyl or phenyl substituted by one or two substituents selected from the group consisting of $C_{1-4}$alkyl, $C_{1-4}$alkoxy, benzyloxy and halo,
each $R_{47}$ is independently halo or $C_{1-4}$alkyl,

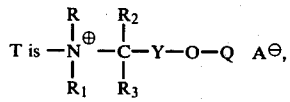

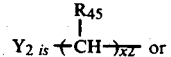 or

, wherein each $R_{45}$ is independently hydrogen or hydroxy,
x2 is 1 or 2, and
x2' is 2 or 3,
q is 0, 1 or 2, and
s is 1 or 2, and each of $R_{43}$ and $R_{44}$ is independently hydrogen, halo, nitro, amino, hydroxy, $C_{1-4}$alkylamino, di-($C_{1-4}$alkyl)amino, phenylamino, phenoxy or cyclohexylamino,
with the proviso that the molecule contains one or two T groups.

46. A dye according to claim 45
wherein R is $C_{1-4}$alkyl,
$R_1$ is $C_{1-4}$alkyl,
$R_2$ is hydrogen or methyl,
$R_3$ is hydrogen or methyl,
Q is phenyl; naphthyl; biphenylyl; dibenzofuranyl; phenyl substituted by halo, $C_{1-4}$alkyl, $C_{1-4}$alkoxy, trifluoromethyl, cyano or nitro or phenyl substituted by 2 to 5 chloro substituents, and

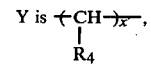

—CH=CH—CH$_2$—, —C≡C—CH$_2$— or —CH$_2$—O—CH$_2$—CH$_2$—,
wherein each $R_4$ is independently hydrogen or $C_{1-4}$alkyl, and
x' is 1, 2 or 3.

47. A dye according to claim 46
wherein R is methyl or ethyl,
$R_1$ is methyl or ethyl,
$R_2$ is hydrogen,
$R_3$ is hydrogen,
Q is phenyl, phenyl substituted by 1 to 5 chloro substituents or 2-naphthyl, and
Y is —CH$_2$—.

48. A dye according to claim 45 having a single T group.

49. A dye according to claim 44 having the formula

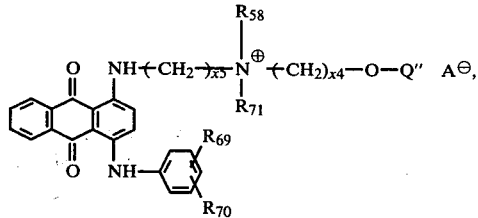

wherein $R_{58}$ is $C_{1-4}$alkyl,
$R_{69}$ is hydrogen, $C_{1-4}$alkyl, $C_{1-4}$alkoxy, benzyloxy or halo,
$R_{70}$ is hydrogen, $C_{1-4}$alkyl, $C_{1-4}$alkoxy or halo,
$R_{71}$ is methyl or ethyl,
Q" is phenyl, biphenylyl, naphthyl, dibenzofuranyl or phenyl substituted by halo, cyano or nitro,
x4 is 2, 3 or 4,
x5 is 2 or 3, and
A$^\ominus$ is an anion.

50. A dye according to claim 44 having the formula

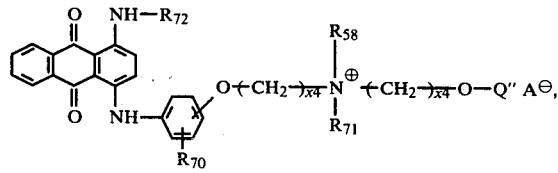

wherein $R_{58}$ is $C_{1-4}$alkyl, $R_{70}$ is hydrogen, $C_{1-4}$alkyl, $C_{1-4}$alkoxy or halo,
$R_{71}$ is methyl or ethyl,
$R_{72}$ is hydrogen, $C_{1-4}$alkyl or cyclohexyl,
Q" is phenyl, biphenylyl, naphthyl, dibenzofuranyl or phenyl substituted by halo, cyano or nitro,
each $x4$ is independently 2, 3 or 4, and
$A^{\ominus}$ is an anion.

51. A dye according to claim 44 having the formula

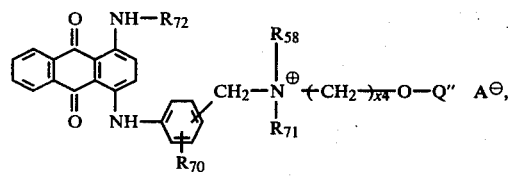

wherein $R_{58}$ is $C_{1-4}$alkyl,
$R_{70}$ is hydrogen, $C_{1-4}$alkyl, $C_{1-4}$alkoxy or halo,
$R_{71}$ is methyl or ethyl,
$R_{72}$ is hydrogen, $C_{1-4}$alkyl or cyclohexyl,
Q" is phenyl, biphenylyl, naphthyl, dibenzofuranyl or phenyl substituted by halo, cyano or nitro,
$x4$ is 2, 3 or 4, and
$A^{\ominus}$ is an anion.

52. A dye according to claim 44 having the formula

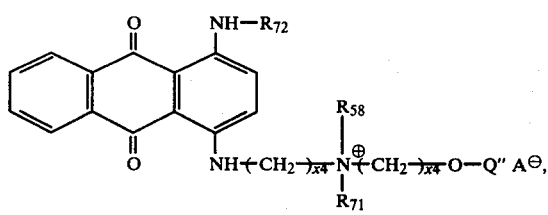

wherein $R_{58}$ is $C_{1-4}$alkyl,
$R_{71}$ is methyl or ethyl,
$R_{72}$ is hydrogen, $C_{1-4}$alkyl or cyclohexyl,
Q" is phenyl, biphenylyl, naphthyl, dibenzofuranyl or phenyl substituted by halo, cyano or nitro,
each $x4$ is independently 2, 3 or 4, and
$A^{\ominus}$ is an anion.

53. A dye according to claim 44 having the formula

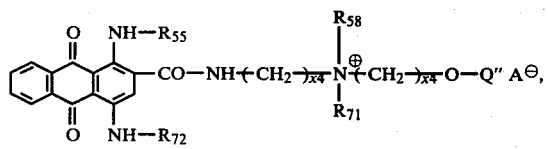

wherein $R_{55}$ is hydrogen or methyl,
$R_{58}$ is $C_{1-4}$alkyl,
$R_{71}$ is methyl or ethyl,
$R_{72}$ is hydrogen, $C_{1-4}$alkyl or cyclohexyl,
Q" is phenyl, biphenylyl, naphthyl, dibenzofuranyl or phenyl substituted by halo, cyano or nitro,
each $x4$ is independently 2, 3 or 4, and
$A^{\ominus}$ is an anion.

54. A dye according to claim 53 having the formula

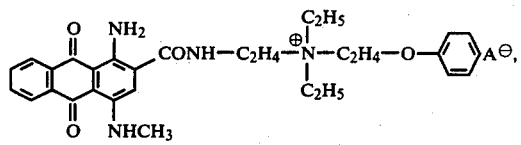

wherein $A^{\ominus}$ is an anion.

55. A dye according to claim 44 having the formula

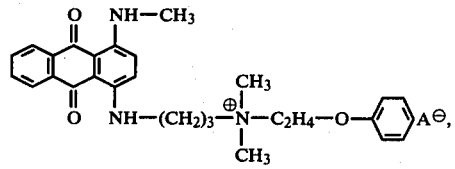

wherein $A^{\ominus}$ is an anion.

56. A dye according to claim 44 having the formula

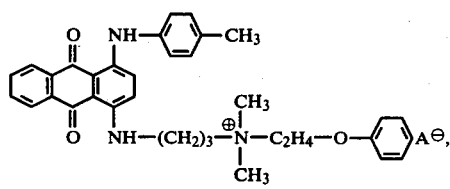

wherein $A^{\ominus}$ is an anion.

57. A dye according to claim 44 having the formula

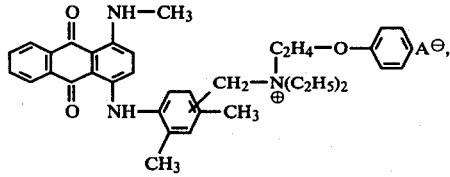

wherein $A^{\ominus}$ is an anion.

58. A dye according to claim 44 having the formula

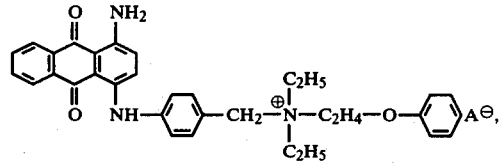

wherein $A^{\ominus}$ is an anion.

59. A dye according to claim 44 having the formula

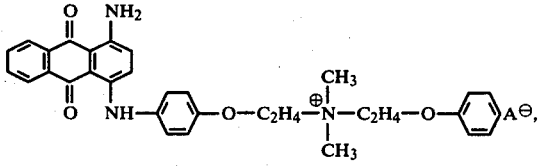

wherein $A^{\ominus}$ is an anion.

60. A dye according to claim 44 having the formula

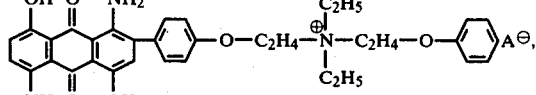

wherein $A^{\ominus}$ is an anion.

* * * * *